United States Patent [19]

Horii et al.

[11] Patent Number: 4,463,172

[45] Date of Patent: Jul. 31, 1984

[54] PROCESS FOR PRODUCING 2-METHYL CEPHEM-2-EM AND 2-METHYLCEPHEM-3-EM DERIVITAVES

[75] Inventors: Satoshi Horii, Sakai; Nariakira Mizokami, Toyonaka; Yutaka Kuwada, Ashiya, all of Japan

[73] Assignee: Takeda Chemical Industries, Ltd., Osaka, Japan

[21] Appl. No.: 235,998

[22] Filed: Feb. 19, 1981

[30] Foreign Application Priority Data

Feb. 25, 1980 [JP] Japan .................................. 55-22951

[51] Int. Cl.³ .................. C07D 501/04; A61K 31/545
[52] U.S. Cl. ..................................... 544/027; 544/16; 544/26; 544/28; 544/29; 544/30; 424/246
[58] Field of Search ....................... 544/26, 27, 21, 30, 544/28, 29; 424/246

[56] References Cited

U.S. PATENT DOCUMENTS

| | | | |
|---|---|---|---|
| 3,647,786 | 3/1972 | Cooper | 544/30 |
| 3,660,396 | 5/1972 | Wright | 544/30 |
| 3,819,621 | 6/1974 | Morimoto et al. | 544/30 |
| 4,144,391 | 3/1979 | Hatfield | 544/27 |
| 4,278,793 | 7/1981 | Dsrchheimer et al. | 544/25 |
| 4,317,907 | 3/1982 | Saikawa et al. | 544/21 |

*Primary Examiner*—Nicholas S. Rizzo
*Attorney, Agent, or Firm*—Antonelli, Terry & Wands

[57] ABSTRACT

Novel 2-methylcephalosporin derivatives and production thereof. These cephalosporin derivatives exhibit excellent antibacterial activities against gram-positive and gram-negative bacteria, thus being of value as a prophylactic or therapeutic agent for infections observed in man and animals.

15 Claims, No Drawings

PROCESS FOR PRODUCING 2-METHYL CEPHEM-2-EM AND 2-METHYLCEPHEM-3-EM DERIVITAVES

The present invention relates to novel 2-methylcephalosporin derivatives and to a process for producing the same.

In more particular, the present invention relates to:
(1) A ceph-2- or 3-em derivative of the general formula:

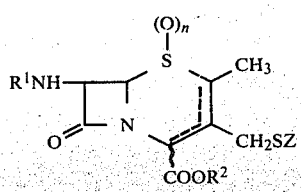

wherein $R^1$ is hydrogen or an acyl group derivable from an organic carboxylic acid; —$COOR^2$ is a carboxyl group which may be esterified; Z is a heterocyclic group which may be substituted; and n is 0 or 1; or a salt thereof, (2) A ceph-2-em derivative of the general formula:

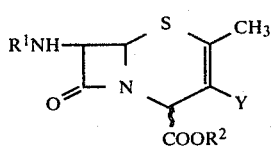

wherein $R^1$ is hydrogen or an acyl group derivable from an organic carboxylic acid; —$COOR^2$ is a carboxyl group which may be esterified; and Y is acetoxymethyl, formyloxymethyl, hydroxymethyl or formyl; or a salt thereof, (3) A 2,3-diexomethylenecepham derivative of the general formula:

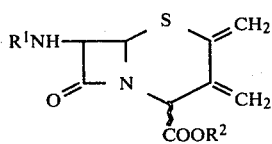

wherein $R^1$ is hydrogen or an acyl group derivable from an organic carboxylic acid; and —$COOR^2$ is a carboxyl group which may be esterified; or a salt thereof, (4) A process for producing a ceph-2-em derivative of the general formula:

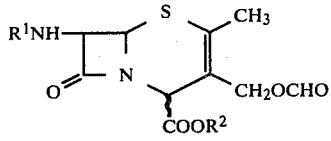

wherein $R^1$ is hydrogen or acyl group derivable from an organic carboxylic acid and —$COOR^2$ is a carboxyl group which may be esterified; or a salt thereof, which comprises treating a ceph-3-em derivative of the general formula:

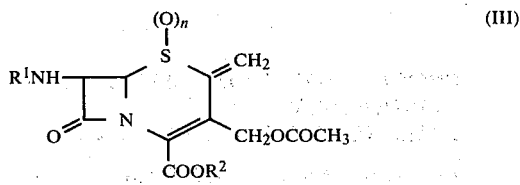

wherein $R^1$ and —$COOR^2$ have the same meaning as above and n is 0 or 1; or a salt thereof with zinc-formic acid, (5) A process for producing a ceph-2-em derivative of the general formula:

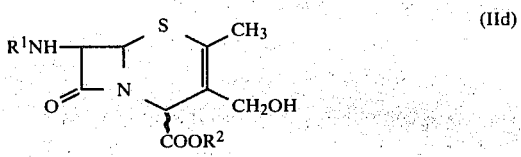

wherein $R^1$ is hydrogen or an acyl group derivable from an organic carboxylic acid; —$COOR^2$ is a carboxyl group which may be esterified, or a salt thereof, which comprises hydrolyzing under acid conditions a ceph-2-em derivative of the general formula:

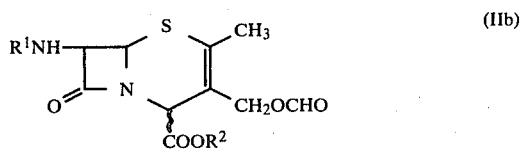

wherein $R^1$ and —$COOR^2$ have the same meaning as above, or a salt thereof, (6) A process for producing a ceph-2-em derivative of the general formula:

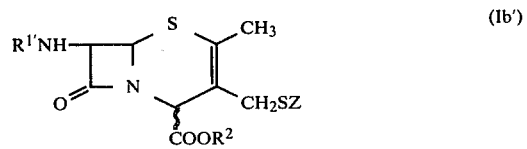

wherein $R^{1'}$ is an acyl group derivable from an organic carboxylic acid; —$COOR^2$ is a carboxyl group which may be esterified; and Z is a heterocyclic group which may be substituted; or a salt thereof, which comprises reacting a ceph-2-em derivative of the general formula:

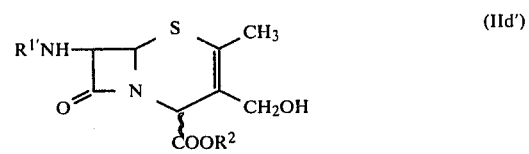

wherein $R^{1'}$ and —$COOR^2$ have the same meaning as above, or a salt thereof with a halogenating agent, and then with a heterocyclic thiol compound which may be substituted or a salt thereof, (7) A process for producing a ceph-3-em derivative of the general formula:

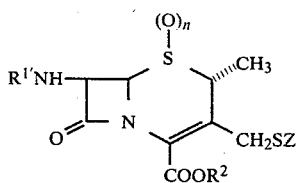

wherein $R^{1'}$ is an acyl group derivable from an organic carboxylic acid; —$COOR^2$ is a carboxyl group which may be esterified; Z is a heterocyclic group which may be substituted, and n is 0 or 1; or a salt thereof, which comprises oxidizing a ceph-2-em derivative of the general formula:

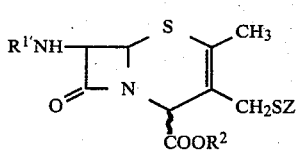

wherein $R^{1'}$, —$COOR^2$ and Z have the same meaning as above, or a salt thereof, (8) A process for producing a ceph-2-em derivative of the general formula:

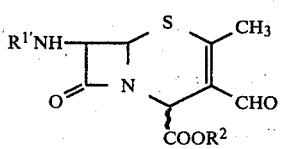

wherein $R^{1'}$ is an acyl group derivable from an organic carboxylic acid; —$COOR^2$ is a carboxyl group which may be esterified; or a salt thereof, which comprises oxidizing a ceph-2-em derivative, of the general formula:

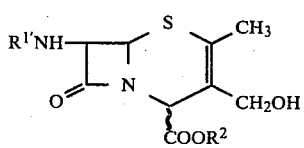

wherein $R^{1'}$ and —$COOR^2$ have the same meaning as above, or a salt thereof, (9) A process for producing 2-α-methyl-3-formylceph-3-em-1-oxide derivative of the general formula:

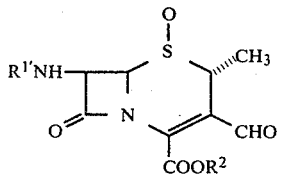

wherein $R^{1'}$ is an acyl group derivable from an organic carboxylic acid, —$COOR^2$ is a carboxyl group which may be esterified, or a salt thereof, which comprises oxidizing a ceph-2-em derivative of the general formula:

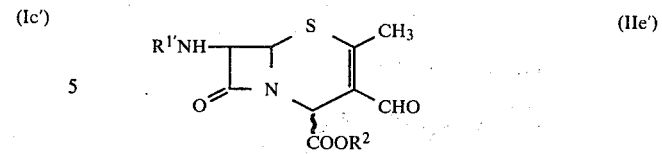

wherein $R^{1'}$ and —$COOR^2$ have the same meaning as above, or a salt thereof,

(10) A process for producing a ceph-2-em derivative of the general formula:

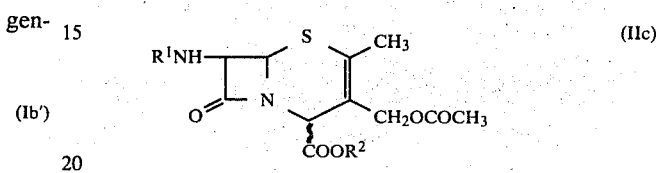

wherein $R^1$ is an acyl group derivable from an organic carboxylic acid; —$COOR^2$ is a carboxyl group which may be esterified; or a salt thereof, which comprises reacting a ceph-3-em derivative of the general formula:

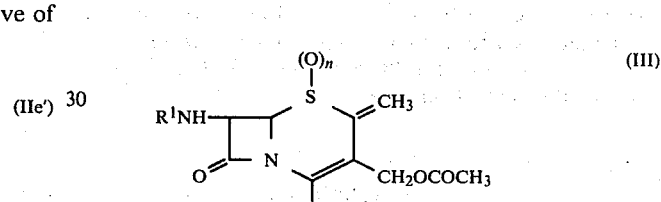

wherein $R^1$ and —$COOR^2$ have the same meaning as above and n is 0 or 1; or a salt thereof with an alkalimetal borohydride,

(11) A process for producing a 2β-methyl-3-acetoxymethylceph-3-em derivative of the general formula:

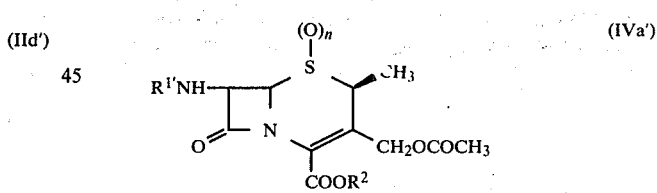

wherein $R^{1'}$ is acyl group derivable from an organic carboxylic acid; —$COOR^2$ is a carboxyl group which may be esterified; and n is 0 or 1; or a salt thereof, which comprises oxidizing a ceph-2-em derivative of the general formula:

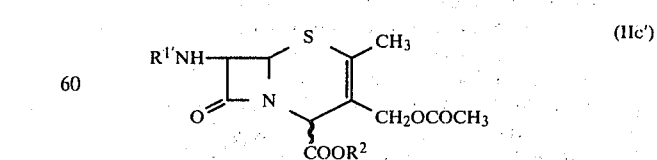

wherein $R^{1'}$ and —$COOR^2$ have the same meaning as above, or a salt thereof,

(12) A process for producing a ceph-3-em derivative of the general formula:

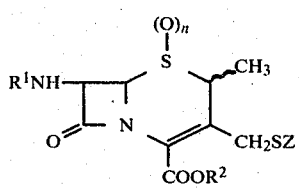

(Ia)

wherein $R^1$ is hydrogen or an acyl group derivable from an organic carboxylic acid; —$COOR^2$ is carboxyl group which may be esterified; Z is a heterocyclic group which may be substituted; and n is 0 or 1; or a salt thereof, which comprises reacting a ceph-3-em derivative of the general formula:

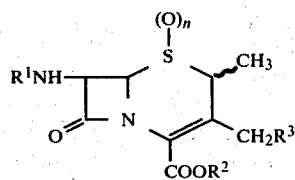

(IV)

wherein $R^1$, —$COOR^2$ have the same meaning as above; $R^3$ is halogen, carbamoyloxy or acyloxy group; n is 0 or 1; or a salt thereof with a heterocyclic thiol compound which may be substituted or a salt thereof, (13) A process for producing a ceph-2- or -3-em-derivative of the general formula:

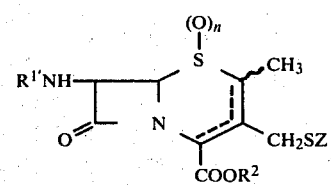

(I')

wherein $R^{1'}$ is an acyl group derivable from an organic carboxylic acid; —$COOR^2$ is a carboxyl group which may be esterified; Z is heterocyclic group which may be substituted; and n is 0 or 1; or a salt thereof, which comprises acylating a ceph-2- or -3-em derivative of the general formula:

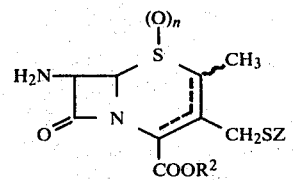

wherein —$COOR^2$; Z and n have the same meaning as above, or a salt thereof.

As regards 2-methylceph-3-em derivatives, the compounds having halogen, a lower alkyl group, an alkoxy group or an acyloxy group in the 3-position were reported in Japanese Published Unexamined Patent Application No. 137988/'78, while 2α- and 2β-3-dimethylceph-3-em derivatives were presented in Journal of Medicinal Chemistry, vol. 14, p. 420 (1971) and Japanese Published Unexamined Patent Application No. 2284/'71.

There were also reported 2-methylceph-3-em derivatives having no substituent group in the 3-position in Recent Advances in the Chemistry of β-Lactam Antibiotics, p. 214 (1976), Journal of the American Chemical Society, 98, 2342 (1976), etc.

However, the 2-methyl-3-heterocyclic thiomethylceph-2-em derivatives or 2α- and 2β-methyl-3-heterocyclic thiomethylceph-3-em derivatives of the general formula (I), the 2-methyl-3-acyloxymethyl, -hydroxymethyl or -formylceph-2-em derivatives of the general formula (II) and the 2,3-diexomethylenecepham derivatives of the general formula (VI) are novel compounds which have not been disclosed in the literature.

The present inventors discovered that the novel ceph-2-em derivatives of the general formula (II) and the novel cepham derivatives of the general formula (VI) can be synthesized from the 2-exomethyleneceph-3-em derivatives of the general formula (III), that the ceph-2-em derivatives of the general formula (II) can then be introduced arbitrarily into the 2-methylceph-2-em derivatives, 2α-methyl, and 2β-methylceph-3-em derivatives of the general formula (I), and that these cephalosporin derivatives exhibit the excellent antibacterial activities against gram-positive and gram-negative bacteria, thus being of value as a prophylactic or therapeutic agent for infections observed in man and animals, followed by further investigation, which has culminated in the present invention as described above.

The acyl groups represented by $R^1$ in each of the formulas described above, which are operable, include the acyl groups derivable from straight-chain or branched, cyclic or non-cyclic organic carboxylic acids which may contain the unsaturated bond, nitrogen, oxygen and sulfur atoms, etc., and generally operable are for example the acyl groups constituting the acylamino groups which are substituted in the 6-position of penicillin derivatives and the 7-position of cephalosporin derivatives. In more detail, examples of such organic carboxylic acid include organic acids such as straight-chain, branched or cyclic aliphatic carboxylic acids including or not including oxygen or sulfur atom in the saturated or unsaturated carbon chain and such aliphatic carboxylic acids having aromatic hydrocarbon residue or heterocyclic group bonded thereto through or not through an oxygen atom or a sulfur atom, e.g. aromatic aliphatic carboxylic acids, aromatic-oxy-aliphatic carboxylic acids, aromatic-thio-aliphatic carboxylic acids, heterocyclic-substituted aliphatic carboxylic acids, heterocyclic-oxy-aliphatic carboxylic acids and heterocyclic-thio-aliphatic carboxylic acids, as well as aromatic carboxylic acids and heterocyclic carboxylic acids. As examples of the aliphatic carboxylic acid described above, there may be mentioned formic acid, acetic acid, propionic acid, butanoic acid, isobutanoic acid, pentanoic acid, isopentanoic acid, pivalic acid, hexanoic acid, cyclohexylcarboxylic acid, acrylic acid, crotonic acid, cyclopentylacetic acid, cyclohexylacetic acid, cycloheptylacetic acid, cyclohexylpropionic acid, cyclohexylacetic acid, cyclohexadienylacetic acid, methoxyacetic acid, cyclohexyloxyacetic acid, methylthioacetic acid, etc. Examples of the aromatic group in the above-mentioned organic carboxylic acids include phenyl, naphthyl, tolyl, xylyl, mesityl and cumenyl. The heterocyclic group in the above-mentioned organic carboxylic acids may be exemplified by residues of saturated or unsaturated, monocyclic or polycyclic heterocyclic compounds containing not less than one heteroatom in the ring, such as furan, thiophene, pyrrole, pyrazol, imidazole, triazole, thiazole, isothiazole, 2-iminothiazoline, 2-oxothiazoline, methylene-1,3- dithiethane, 2,3-dihydro-1,4-oxathiin, 1,4-dithianaphthalene, dihydro-1,3-dithiin, oxazole, isoxazole, thiadiazole, oxadiazole, thiatriazole, oxatriazole, tetrazole, pyridine, pyradine, pyrimidine, pyridazine, benzothiophene, benzofuran, indole, indazole, benzimidazole, benzothiadiazole, benzoxazole, purine, quinoline, isoquinoline, phthalazine, naphthylidine, quinoxaline, quinazoline, pyrrolidine, imidazolidine, piperidine and piperazine. Further, the aliphatic groups, aromatic hydrocarbon residues and heterocyclic groups which consist of these organic carboxylic acids may have, in arbitrary positions, one or more appropriate substituents such as halogens, hydroxyl, sulfo, mercapto, carboxyl, alkyl, alkoxyl, alkylthio, amino, alkylamino, dialkylamino, cyano, alkanoyl, aralkanoyl, arylcarbonyl, alkanesulfonylamino, alkanoyloxy, aralkanoyloxy, arylcarbonyloxy, hydroxyimino, alkoxyimino, oxo, thioxo, ureido, carbamoyl and amidino groups. Of such substituents, the hydroxyl, carboxyl and amino groups, if necessary, may each be protected further by suitable protective groups which are normally employed in the fields of cephalosporin, penicillin and peptide chemistry, as being described hereinafter.

As the above mentioned acyl group, use is made of easily removable protective groups for the amino group employed in the peptide chemistry, such as alkoxycarbonyl group, e.g. tert-butoxycarbonyl, iso-bornyloxycarbonyl, etc., and aralkyloxycarbonyl group e.g. benzyloxycarbonyl, p-nitrobenzyloxycarbonyl, p-methoxybenzyloxycarbonyl, etc. In addition, those protected with any of the easily removable protective groups for the amino group other than the above-mentioned ones, as described by J. W. Barton in the chapter 2 of the publication edited by J. F. W. McOmie ["Protective groups in Organic Chemistry"; Plenum Press, N.Y. (1973)], are regarded as the above-mentioned acyl group as well. Furthermore, $R^{1'}$, except that it does not include hydrogen, indicates the same definition as $R^1$.

Referring more specifically to examples of the acyl groups represented by $R^1$ which are desirable as antibacterial compounds, there may be mentioned;

$R^1$ being groups of $R^4$—$R^5$—$CH_2$—CO—
[wherein $R^4$ is cyano, a phenyl group which may be substituted, a heterocyclic group which may be substituted, a lower alkyl group which may be substituted or an amidino group which may be substituted; $R^5$ is a mere linkage or —S—], $R^1$ being groups of

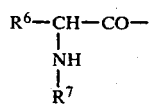

[wherein $R^6$ is a phenyl group which may be substituted, a heterocyclic group which may be substituted or a cycloalkenyl group; $R^7$ is hydrogen, a protective group for the amino group, a carbamoyl group which may be substituted, or a group represented by $R^8$—CO— (wherein $R^8$ is a heterocyclic group which may be substituted)], $R^1$ being groups of

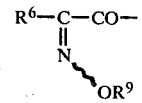

[wherein $R^6$ is a phenyl group which may be substituted, a heterocyclic group which may substituted or a cycloalkenyl group; $R^9$ is hydrogen, a lower alkyl group or the formula of —$R^{10}$—$R^{11}$ (wherein $R^{10}$ is a lower alkylene or lower alkenylene; $R^{11}$ is carboxyl or its ester)], $R^1$ being groups of

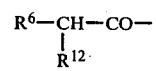

[wherein $R^6$ is a phenyl group which may be substituted, a heterocyclic group which may be substituted or a cycloalkenyl group; $R^{12}$ is a hydroxy, formyloxy, carboxy or sulfo group], etc.

Referring to the above formulas, examples of the substituent on the phenyl group represented by $R^4$ which may be substituted include, lower alkyl group having 1 to 3 carbon atoms, lower alkoxy groups having 1 to 3 carbon atoms, halogen, nitro, amino, hydroxy, aminomethyl, lower-alkylsulfonylamino, etc.

As examples of the heterocyclic group in the heterocyclic group represented by $R^4$ which may be substituted, there may be mentioned heterocyclic groups inclusive of 5- to 6-membered heterocyclic groups having 1 sulfur atom or 1 to 4 nitrogen atoms which contain one sulfur and nitrogen atom. As specific examples of such heterocyclic group, there may be mentioned 2-thienyl, 3-thienyl, 2-pyridyl, 3-pyridyl, 4-pyridyl, 4-pyridonyl, 2-thiazolyl, 4-thiazolyl, 5-thiazolyl, isothiazolyl, 1-tetrazolyl, 5-tetrazolyl, etc.

Examples of the substituent group in the heterocyclic group represented by $R^4$ which may be substituted include lower alkyl having 1 to 3 carbon atoms, lower alkoxy having 1 to 3 carbon atoms, halogen, nitro, hydroxy, amino, carboxy, oxo, etc.

The lower alkyl represented by $R^4$ which may be substituted is preferably lower alkyl having 1 to 3 carbon atoms, and examples of such substituent group include halogen, hydroxy, cyano, carboxy, etc.

As examples of the amidino group represented by $R^4$ which may be substituted, there may be mentioned amidino groups wherein the $N^1$ atom may be linked to $R^5$ or the atom C may be linked to $R^5$, $N^1$ and $N^2$ may form a ring through a lower alkylene having 2 to 4 carbon atoms, the atoms $N^1$ and $N^2$ may be substituted by lower alkyl groups, and the C atom may be substituted by a lower alkyl or aralkyl group in the case of the $N^1$ atom being bonded to $R^5$.

As examples of the heterocyclic group in the heterocyclic group represented by $R^6$ which may be substituted, there may be mentioned 5-membered heterocyclic groups having one nitrogen, sulfur or oxygen atom, which contain, or do not contain, nitrogen atoms. Specific examples of such heterocyclic groups include 2-thiazolyl, 4-thiazolyl, 5-thiazolyl, 2-thienyl, 3-thienyl, 2-furyl and 3-furyl.

As examples of the substituent in the heterocyclic group represented by $R^6$ which may be substituted, there may be mentioned lower alkyl groups having 1 to 3 carbon atoms, lower alkoxy having 1 to 3 carbon atoms, hydroxy, halogen, amino, etc.

As examples of the phenyl group represented by $R^6$ which may be substituted, there may be mentioned lower alkyl groups having 1 to 3 carbon atoms, lower alkoxy groups having 1 to 3 carbon atoms, halogen, nitro, amino, hydroxy, lower alkylsulfonylamino, etc.

As examples of the cycloalkenyl group represented by $R^6$, there may be mentioned cycloalkenyl groups having 5 to 6 carbon atoms, and preferably, cyclohexadienyl, cyclohexenyl, etc.

As examples of the substituent in the carbamoyl group represented by $R^7$ which may be substituted, these may be mentioned lower alkyl groups having 1 to 3 carbon atoms, amidino group which may be substituted, cyanomethyl, etc.

As examples of the heterocyclic group in the heterocyclic group represented by $R^8$ which may be substituted, there may be mentioned 5- to 6-membered heterocyclic groups having one nitrogen, oxygen or sulfur atom, 5- to 6-membered heterocyclic groups having 2 to 3 nitrogen atoms, and 5- to 6-membered heterocyclic groups having one each of nitrogen and sulfur atom, whereby these heterocyclic groups may be condensed mutually or with benzene rings.

Specific examples of the heterocyclic group represented by $R^8$ as described above include pyrrolyl, furyl, thienyl, pyridyl, pyranyl, thiopyranyl, pyrimidyl, piradinyl, piridazinyl, piperazinyl, imidazolizinyl, thiazolyl, isothiazolyl, triazinyl, quinolyl, isoquinolyl, naphthylidyl, benzopyranyl, pyrido[2,3-d]pyrimidyl, thieno[2,3-b]pyridyl, pyridazino[2,3-a]pyrimidyl, etc.

As examples of the substituent in the heterocyclic group represented by $R^8$ which may be substituted, there may be mentioned lower alkyl groups having 1 to 3 carbon atoms, lower alkoxy groups having 1 to 3 carbon atoms, hydroxy, oxo, thioxo, formyl, amino, halogen, lower alkylsulfonyl having 1 to 3 carbon atoms, furfurylideneamino, etc.

Preferred examples of the lower alkyl represented by $R^9$ are those having 1 to 3 carbon atoms.

Preferred examples of the lower alkylene of $R^{10}$ in the group represented by the formula $-R^{10}-R^{11}$ in $R^9$ include those having 1 to 3 carbon atoms, such as methylene, ethylene, propylene and isopropylene, while preferred examples of the alkenylene represented by $R^{11}$ include those having 1 to 3 carbon atoms, such as propenylene and vinylene. As examples of the ester of carboxy represented by $R^{11}$, there may be mentioned methyl ester, ethyl ester, propyl ester, etc.

Specific examples of the lower alkyl groups in the above formulas include methyl, trifluoromethyl, ethyl, n-propyl, isopropyl, n-butyl, isobutyl, sec-butyl, tert-butyl, pentyl, isopentyl, hexyl, isohexyl, etc.

Specific examples of the lower alkyl group having 1 to 3 carbon atoms include methyl, trifluoromethyl, ethyl, n-propyl, isopropyl, etc., while specific examples of the lower alkoxy groups having 1 to 3 carbon atoms include methoxy, ethoxy, n-propoxy, isopropoxy, etc.

As specific examples of the halogen, there may be mentioned fluorine, chlorine, bromine and iodine.

As specific examples of the lower alkylsulfonyl, there may be mentioned methylsulfonyl, ethylsulfonyl, n-propylsulfonyl, isopropylsulfonyl, etc. $-COOR^2$ represents carboxyl group which may be esterified, and the carboxyl group which may be esterified designates a carboxyl group or an esterified carboxyl group. In this case, the carboxyl group may form a salt.

Examples of the ester residue of the esterified carboxyl group are tert-butyl, 2,2,2-trichloroethyl, benzyl, p-methoxybenzyl, p-nitrobenzyl, trityl, benzhydryl, bis(p-methoxyphenyl)methyl, phenacyl, 2-methylthioethyl, trimethylsilyl, dimethylsilyl, etc., and further include alkoxymethyl groups such as methoxymethyl, ethoxymethyl, isopropoxymethyl, etc., 1-alkoxyethyl groups such as 1-methoxyethyl, 1-ethoxyethyl, etc., alkylthiomethyl groups such as methylthiomethyl, ethylthiomethyl, iso-propylthiomethyl, etc., acyloxymethyl groups such as acetoxymethyl, pivaloyloxymethyl, etc., 1-acyloxyethyl groups such as 1-n-propionyloxyethyl, etc., 1-alkoxycarbonyloxyethyl groups such as 1-ethoxycarbonyloxyethyl, etc., and phthalidyl groups, etc., the last four groups being capable of forming biologically active ester derivatives, such as pivaloyloxymethyl exhibiting the effects of increasing blood levels and prolonging the effective period. Further, the easily removable protective groups for the carboxyl group other than the above-mentioned, as described by E. Haslam in the chapter 5 of the publication edited by McOmie, can also be employed as such ester residue.

The compounds of the present invention as represented by the general formulas (I) to (VI) may present the form of pharmacologically allowable salts generally known in the fields of cephalosporins and penicillins. Thus, in cases in which an acid group such as a carboxyl and sulfo group is present in the molecule, for example, in the case of $-COOR^2$ in the 4-position being a carboxyl group, the compounds may form salts with inorganic bases such as alkali metals, e.g. sodium, potassium, lithium, etc., and alkaline earth metals, e.g. calcium, magnesium, etc., basic amino acids such as arginine, ornithine, lysine and histidine, and organic bases such as dimethylamine, dicyclohexylamine, trimethylamine, diethanolamine, di-n-butylamine, etc.

$R^3$ represents halogen, carbamoyloxy and acyloxy group. While as the halogen may be mentioned fluorine, chlorine, bromine and iodine, examples of the reactive acyloxy group include alkylcarbonyloxy groups having 2 to 4 carbon atoms such as acetyloxy and propionyloxy, phenylacetyloxy groups which may be substituted by hydroxyl, sulfo, amino, etc. at the α-position such as mandeloxy, α-sulfophenylacetyloxy, glycyloxy, and phenylacetyloxy, carboxyl-substituted alkylcarbonyloxy groups having 2 to 4 carbon atoms such as succinoyloxy, groups of the general formula:

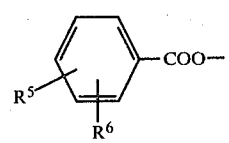

[wherein $R^5$ and $R^6$ each represent a hydrogen atom, a carboxyl, carboethoxycarbamoyl, carboethoxysulfamoyl or nitro group] such as 2-carboxybenzoyloxy, 2-(carboethoxycarbamoyl)benzoyloxy, 2-(2-carboethoxysulfamoyl)benzoyloxy, 2-carboxy-3(or, 4 or 6)nitrobenzoyloxy, 2,4-dicarboxybenzoyloxy, etc. Of them, the preferable are alkylcarbonyloxy groups having 2 to 4 carbon atoms such as acetoxy and propionyloxy, particularly acetoxy.

Z in the general formulas (I), (Ia), (Ib), (Ic), etc. designates heterocyclic groups which may be substituted by arbitrary substituents.

Herein, as examples of the heterocyclic group, there may be mentioned

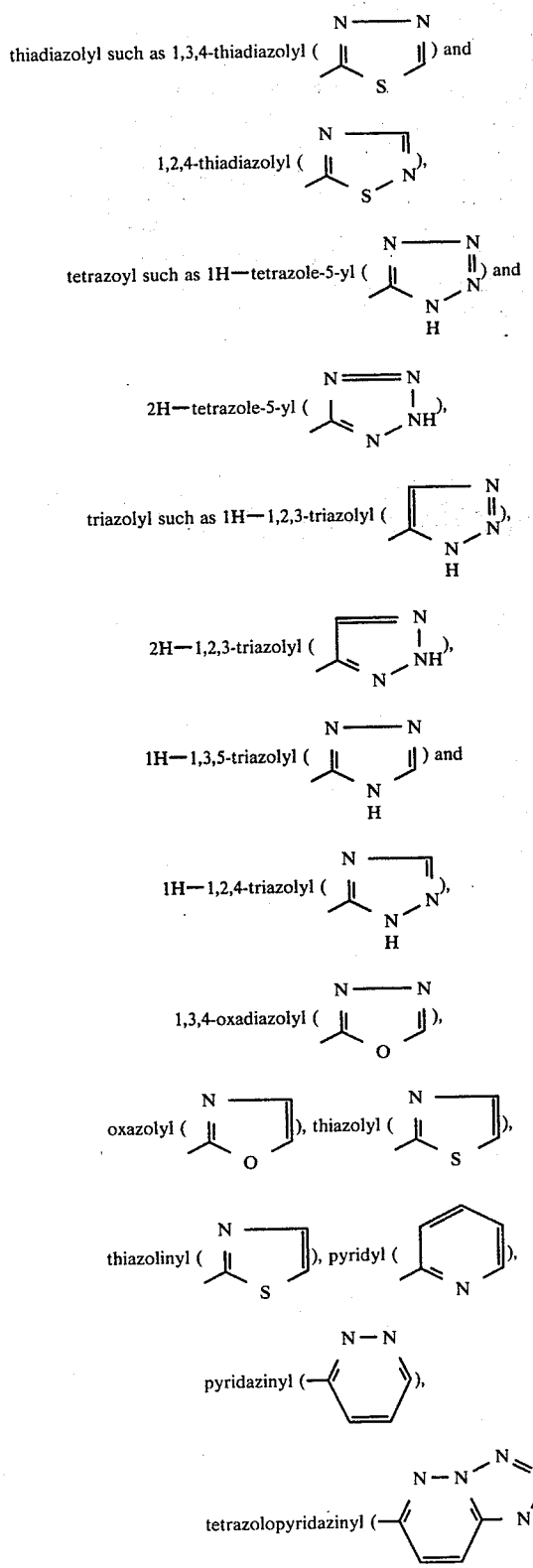

These heterocyclic groups may be substituted by arbitrary substituents. As examples of the arbitrary substituent, there may be specifically mentioned lower alkyls such as methyl and ethyl, lower alkyl groups substituted by hydroxy, carboxy, dimethylamino and sulfo, mercapto group, hydroxy group, amino group, lower alkylthio groups such as methylthio and ethylthio, lower alkoxy groups such as methoxy and ethoxy, and the like. The nitrogen atom of pyridazinyl and pyridinyl groups may be converted into oxido.

In cases in which the group represented by $R^1$ or Z contains a basic nitrogen atom such as amino, imino and amidino, the group may form a salt with an inorganic acid such as hydrochloric acid, sulfuric acid, hydrobromic acid, nitric acid, etc., or an organic acid such as maleic acid, oxalic acid, fumaric acid, p-toluenesulfonic acid, etc.

Furthermore, in cases in which the compound of the present invention possesses an asymmetric carbon atom (particularly in the case of the acyl portion in acylated amino groups of $R^1$ containing an asymmetric carbon atom), there exist the D- and L-optical isomers relative to the asymmetric carbon atom. In cases in which the compound of the present invention has an asymmetric carbon atom, for example, as is the case with the group of $R^1$ being the group represented by the formula:

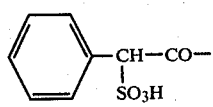

the compound of the present invention contains the D-isomer, L-isomer (R-isomer, S-isomer) and an arbitrary mixture thereof. Further, the compound of the present invention, in some instances, contains geometrical isomers. In cases in which the group of $R^1$ is for example the group represented by the formula:

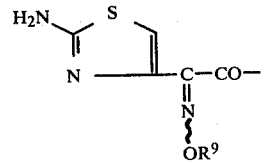

the compound of the present invention contains not only respective geometrical isomers (syn- and anti-isomers) but also a mixture thereof at arbitrary ratios. The above formula is known to be able to produce tautomerism as shown below:

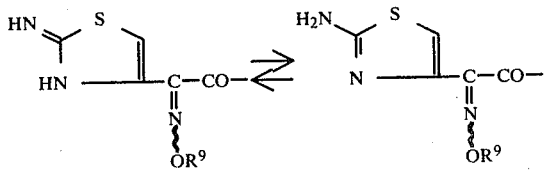

and, both of the tautomers and a mixture thereof at arbitrary ratios fall within the scope of the present invention.

For 2-methylceph-3-em derivatives, there can exist two isomeric forms of 2α-methyl and 2β-methyl isomers. For the 2-methyl-3-heterocyclic-thiomethylceph-3-em derivatives which fall into the scope of the compound of the general formula (I), one of the objective compounds of the present invention, there also exist two isomers, the 2α- and 2β-isomers. For the reason of this, in the above general formulas, the 2α-methyl isomer is designated as CH₃ and the 2β-methyl isomer as CH₃, while the sign, CH₃, is employed to indicate that both isomers are included or any of them may be included. Of the cephalosporin skeleton, the portion indicated by the dotted line in the six-membered ring shows that a double bond is situated in either the 2- or 3-position.

The 2α-methyl isomer can be determined by NMR spectrum, i.e. in the 2α-methyl isomer the Nuclear Overhauser Effect (NOE) is observed between the methyl at the 2-position and the proton at the 6-position of the cephem ring.

The objective compounds of the present invention, (I), (II) and (VI) can be synthesized, for example, from the 2-methyleneceph-3-em derivatives of the general formula (III). As to the compounds of the formulas (I) to (VI), the reaction of converting a compound represented by the formula wherein the $R^1$ is an acyl group derived from an organic acid into a compound represented by the formula wherein the $R^1$ is hydrogen, and the reaction of converting a latter compound into a compound represented by the formula wherein the $R^1$ is another acyl group derived from an organic carboxylic acid can be carried out in the manner per se known for deacylation and acylation of cephalosporin derivatives having no substituent at the 2-position (for example, the former reaction is disclosed in U.K. Patent Application Nos. 1041985 and 1239814, and the latter reaction is described in German Published Patent Application Nos. 2461478 and 2556736.).

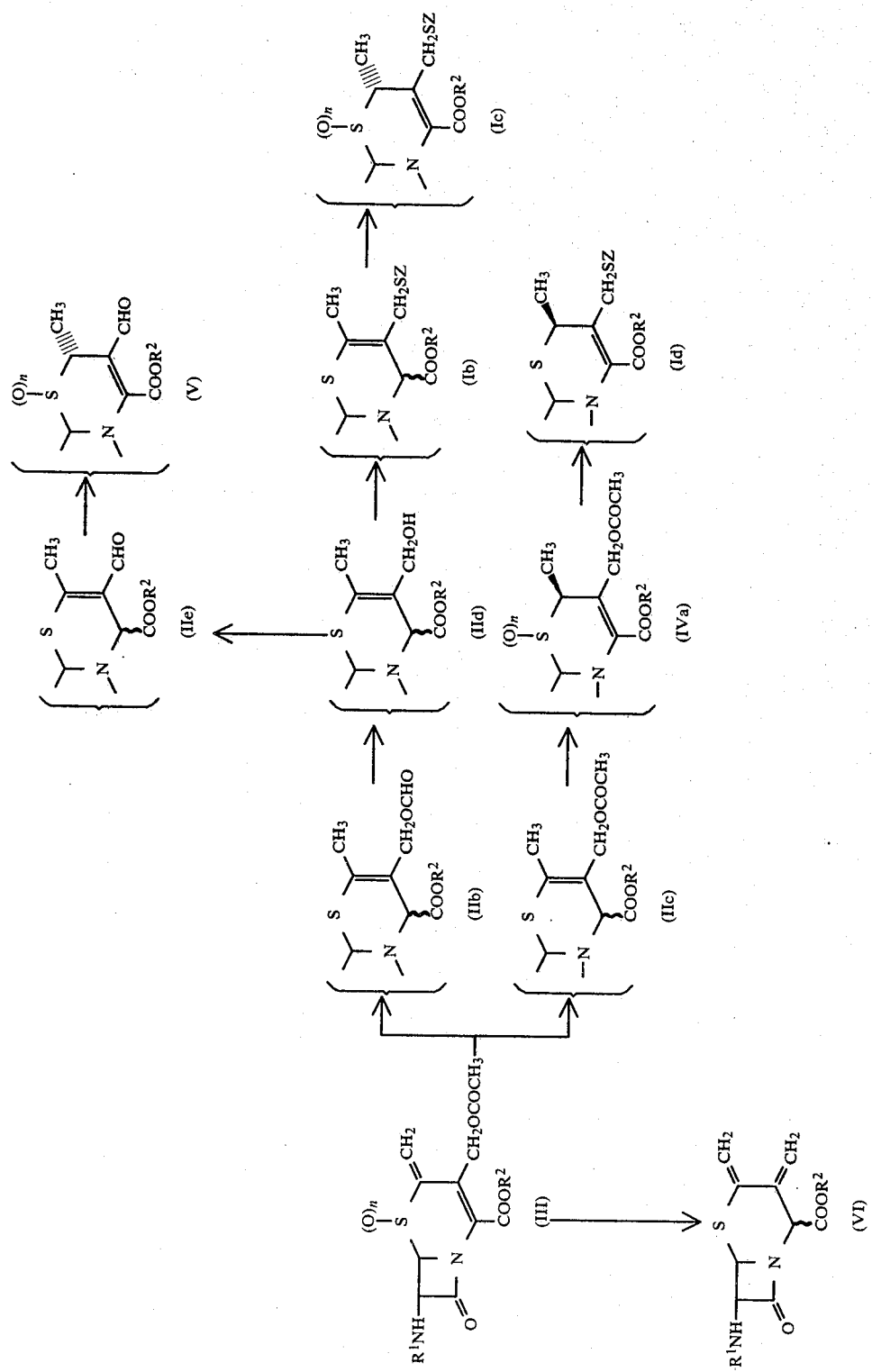

The 2-methyleneceph-3-em derivative (III), which is employed as the foremost starting material, can be synthesized by means of per se known methods by introducing a methylene group into the 2-position of a cephalosporanic acid-1-oxide derivative. Thus, the compound can be synthesized for example by reacting a cephalosporanic acid derivative with formaldehyde or a reactive derivative thereof in an appropriate solvent (e.g. a mixed solvent of dichloromethane and tert-butanol) in the presence of salts of condensates from formaldehyde and primary or secondary amine [e.g. salts of $H_2C=N^+(CH_3)_2$] or salts of amines with acids. The 2-methyl-3-formyloxymethylceph-2-em derivative of the general formula (IIb) can be produced by reacting the compound of the general formula (III) with zinc-formic acid. In this case, formic acid of not less than at least an equimolar amount is desirably added.

The starting compound of the general formula (III) may be either a sulfide (n=0) or a sulfoxide (n=1), but in the case of a sulfoxide, it undergoes simultaneously reduction. In this reaction, formic acid is usable both as a reagent (formate anion source) and a solvent, but an inert solvent such as tetrahydrofuran, dimethylformamide, dimethylacetamide and hexamethylphosphoramide may be used as a solvent, if necessary. Especially, dimethylformamide and hexamethylphosphoramide are preferable in that they accelerate the reaction. The reaction is normally carried out at temperature of −30° C. to room temperature. The concentration of formic acid is preferably 70% or more. In such case, with decreasing concentration of formic acid, 2,3-diexomethylenecepham derivatives of the general formula (VI) are by-produced, resulting in decreased yields of a 2-methyl-3-formyloxymethylceph-2-em derivative.

In this reaction step, utilization of acetic acid in place of formic acid yields only the compound (VI) as the reaction product. The compound (VI) is useful as an intermediate for the synthesis of e.g. 2-methylene-3-methylceph-3-em derivatives and 2-oxo-3-methoxyceph-3-em derivatives.

The hydrolysis from a 2-methyl-3-formyloxymethylceph-2-em derivative (IIb) to a 2-methyl-3-hydroxymethylceph-2-em derivative of the general formula (IId) can be conducted by means of the methods known for the hydrolysis of formyl of 3-formyloxymethylcephem derivatives not having a methyl group in the 2-position. For example, the hydrolysis of (IIb) is conducted under acid conditions. In this case, it is desirably conducted under dilution with a protic solvent such as lower alkanols, preferably an inert solvent such as dimethylformamide, dichloromethane, chloroform, tetrahydrofuran, acetone, dioxane, etc. The acid conditions are desirably not higher than pH 4, advantageously pH 1 to 3. As an acid, use is made of inorganic and organic acids such as hydrochloric acid, sulfuric acid, phosphoric acid, perchloric acid, trifluoroacetic acid, p-toluenesulfonic acid, hydrobromic acid and nitric acid.

The compound (IId) can be produced advantageously by conducting the hydrolysis at a temperature within the range of 0° to 50° C., preferably 15° to 40° C.

In order to derive a 2-methyl-3-heterocyclic-thiomethylceph-2-em derivative of the general formula (Ib') from a compound of the general formula (IId'), for example, the method is employed of reacting (IId') with a halogenating reagent selected from phosphorus trihalides, phosphoryl halides and thionyl halides and reacting the resultant 3-halomethylceph-2-em derivative with a heterocyclic thiol compound of the general formula, HS—Z (VII) (wherein Z is a heterocyclic group which may substituted). The first stage of this reaction step involves production of a 3-halomethylceph-2-em intermediate and comprises reacting a 3-hydroxymethyl derivative (IId') with a halogenating agent selected from phosphorus trihalides, phosphoryl halides and thionyl halides, preferably from phosphorus trichloride, phosphoryl chloride and thionyl chloride. In this case, the halogenating agent of at least 1 mole against 1 mole of (IId') is required to be used. In order to obtain the 3-halomethylceph-2-em intermediate in high yields, however, further excessive amount of the halogenating agent is required, and the halogenating agent is preferably used in quantities 1.2 to 2 times the theoretical ones against 1 mole of (IId'). Moreover, it is useful in increasing the yields to conduct the reaction in the presence of a tertiary amine, such as pyridine and triethylamine, of an amount equimolar with the halogenating agent used. The reaction is conducted in an inert solvent such as acetonitrile, methylene chloride, tetrahydrofuran, acetone and ethyl acetate, whereby such solvents are employed solely or as a mixed solvent. The reaction temperature is conveniently of relatively low temperatures, and the reaction is conducted normally at temperatures of −30° to 20° C., preferably −10° to 0° C. The reaction normally proceeds fast and can be completed within about 30 minutes. The typical reaction time is 5 to 30 minutes. After completion of the reaction, the product is treated by conventional procedures. The resultant 3-halomethylceph-2-em derivative is treated in the subsequent second step, whereby the 3-halomethylceph-2-em derivative is not necessarily required to be isolated in the pure state but the partly purified compound can be generally utilized in the subsequent reaction directly without being further purified. Thus, the 3-halomethylceph-2-em derivative is reacted with a heterocyclic thiol compound of the general formula (VII) of at least equimolar quantities to obtain (Ib'). The reaction is conducted for example in any of inert organic solvents, solely or as a mixed solvent, such as acetonitrile, methylene chloride, tetrahydrofuran, acetone, ethyl acetate, dimethylsulfoxide, dimethylacetamide, dimethylformamide and hexamethylphosphoramide, etc. The reaction is normally conducted at room temperature, but warming may be made to such an extent as not to destroy the reaction product, when the rate of reaction is slow. In this reaction, it is preferable to use the heterocyclic thiol compound in not less than 1.5 times the theoretical quantity against 1 mole of (IId'). The compound (Ib') obtained in this way can be purified and isolated by a conventional procedure. The 2-methyl-3-acetoxymethylceph-2-em derivative of the general formula (IIc) can be produced by treating a 2-exomethylene derivative (III) with an alkali metal borohydride such as sodium borohydride, potassium borohydride, lithium borohydride and sodium trimethoxyborohydride.

In this case, the compound (III) may be either a sulfide (n=0) or a sulfoxide (n=1) but, in the case of (III) being a sulfoxide, reduction of the sulfoxide to the sulfide takes place simultaneously. The reaction is preferably conducted in any of inert solvents, solely or as a mixed solvent, such as methanol, ethanol, 2-propanol, methylene chloride, tetrahydrofuran, dimethyleneglycol monomethyl ether, dimethylformamide, etc. The reaction temperature is desirably in the range of −5° to 5° C. Isomerization of the 2-methylceph-2-em derivatives (Ib'), (IIc') and (IIe') to the 2-methylceph-3-em derivatives (Ic'), (IVa') and (V') can be effected by means of the method already known for a ceph-2-em derivative which permits isomerizing to a ceph-3-em derivative via a ceph-3-em-1-oxide derivative. As an oxidizing agent employed to obtain the 2-methylceph-3-em-1-oxide derivatives (Ic'), (IVa') and (V') [wherein n=1], use is made of organic and inorganic peracids. Specifically as such peracids, use is made for example of percarboxylic acids such as performic acid, peracetic acid, trifluoroperacetic acid, permaleic acid, perbenzoic acid, m-chloroperbenzoic acid, monoperphthalic acid, p-toluenepersulfonic acid, etc. and inorganic peracids such as persulfonic acid, hydrogen peroxide, periodic acid and persulfuric acid, etc. These peracids are utilized solely or as a mixture of two or more peracids. The oxidizing agent is normally utilized in at least an equivalent amount. Preferably, it is utilized in about 10 to 20% excess. Nevertheless, it is possible to employ the oxidizing agent in a large excess of 10-fold quantities or more. The reaction conditions are such relatively mild conditions as the temperature of $-50°$ to $100°$ C., preferably $-10°$ to $40°$ C. If necessary, a reaction-controlling agent such as isopropanol may be allowed to coexist. The oxidation reaction is normally conducted in the presence of an appropriate solvent. Selection of the solvent depents particularly upon the solubility of a starting substance and type of selected oxidizing agent, and, for example, dichloromethane, chloroform, dimethylformamide, tetrahydrofuran, acetonitrile, acetic acid, ethyl acetate, etc. are used solely or as a mixed solvent.

Reduction of the 2-methylceph-3-em-1-oxide derivatives (Ia), (Ic) and (IV) [wherein n=1] to the sulfides (Ia), (Ic) and (IV) [wherein n=0] can be effected by treating with a reducing agent by means of the method already known for reducing a ceph-3-em-1-oxide derivative to the corresponding sulfide. As the reducing agent, use is advantageously made of trihalophosphines such as phosphorus trichloride, phosphorus tribromide, etc., halosilanes such as trichlorosilane, etc., quaternary chloromethyleneiminium salts such as chloromethylenedimethyliminium chloride, etc. The reduction of the sulfoxide can be effected by utilizing, in the presence of acid halides, e.g. specifically such activated reagents as acetyl chloride, anionic reducing agent such as $S_2O_4{}^{2-}$, $I^-$ and ferrocyanide ions, cationic reducing agents such as $Sn^{2+}$, $Fe^{2+}$ and $Cu^+$ ions, trivalent phosphorus compounds such as phosphines and phosphites, and the like, or by means of catalytic reduction with use of transition metal catalysts containing palladium, platinum, rhodium, etc. Such reduction reaction is normally conducted in the presence of a suitable solvent. Selection of the solvent depends particularly upon the solubility of a starting substance and type of selected reducing agent, and, for example, dimethylformamide, tetrahydrofuran, dichloromethane, chloroform, acetonitrile, acetic acid, ethyl acetate, etc. are used solely or as a mixed solvent.

The method of producing a 2β-methyl-3-heterocyclicthiomethylceph-3-em derivative of the general formula:

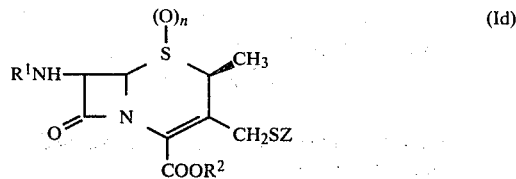

[wherein $R^1$, $-COOR^2$, Z and n are as defined hereinbefore], which comprises reacting a 2β-methyl-3-acetoxymethylceph-3-em derivative of the general formula (IVa) or a salt thereof with a heterocyclic thiol compound of the general formula (VII) or a salt thereof, can be carried out by means of the method already known as the technique of converting a 3-acetoxymethylceph-3-em derivative not having a methyl group in the 2-position into a 3-heterocyclic thiomethyl derivative. Thus, the compound (IVa) is dissolved in water or an aqueous organic solvent at pH 6 to 8, and a heterocyclic thiol compound of the general formula (VII) or a salt thereof is added to the solution to allow them to react. The reaction temperature is in the range of room temperature to 100° C., suitably in the range of 50° to 70° C. The reaction time varies with the reaction temperature, and is 30 minutes to 10 hours. In this case, utilization of a buffer solution yields satisfactory results. In addition, a heterocyclic thiol compound of the general formula (VII) or a salt thereof may be made to act on it in the presence of halides or inorganic salts of metals of Group I and Group II such as potassium iodide, sodium iodide, calcium iodide, barium iodide, sodium chloride, ammonium chloride, barium chloride and magnesium chloride, or in the presence of boron trifluoride or a complex compound thereof.

Oxidation of a 2-methyl-3-hydroxymethylceph-2-em derivative (IId') to a 2-methyl-3-formylceph-2-em derivative (IIe') can be effected by means of the method already known for oxidation of a 3-hydroxymethylceph-2-em derivative without a methyl group in the 2-position to a 3-formylceph-2-em derivative. Thus, the procedure of oxidizing the corresponding (IId') with use of manganese dioxide or chromium trioxide, preferably a reagent consisting of chromium trioxide added in sulfuric acid-water called the Jones reagent and a chromium trioxide.pyridine complex called the Collins reagent, the method of oxidizing with 2,3-dichloro-5,6-dicyano-1,4-benzoquinone, or the procedure of introducing into a 3-halomethyl group and then oxidizing with aliphatic sulfoxides in the presence of a silver compound, etc. are used.

2α-Methyl-3-formylceph-2-em derivatives (IIe) and 2α-methyl-3-formylceph-3-em derivatives (V) can be utilized as starting materials for synthesizing 2α-methyl-3-(O-substituted-oxyiminomethyl)cephem derivatives ($Y^2=-CH=NOR$; $Y^2$ designates a 3-position substituent derived from a formyl group in the 3-position, and R is a suitable substituent) such as 2α-methyl-3-methoxyiminomethylcephem derivatives and 2α-methyl-3-morpholinoethoxyiminomethylcephem derivatives. Furthermore, 2-methyl-3-formylcephem derivatives are compounds useful as starting materials for synthesizing 2-methyl-3-substituted-cephem derivatives such as 2-methyl-3-(2-substituted-vinyl)cephem derivatives ($Y^2=-CH=CH-R$), 2-methyl-3-(3-substituted-hydrazonomethyl)cephem derivatives

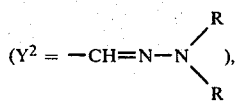

2-methyl-3-(4-substituted-thiosemicarbazono)methylcephem derivatives

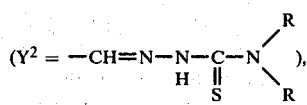

2-methyl-3-(5-substituted-amino-1,3,4-thiadiazole-2-yl)methylcephem derivatives

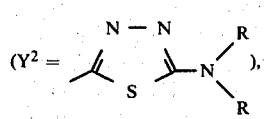

2-methyl-3-carboxycephem derivatives ($Y^2=$ —COOH), 2-methyl-3-cyanocephem derivatives ($Y^2=$ —CN), etc. In cases in which amino (inclusive of basic nitrogen containing groups other than amino group), hydroxyl and carboxyl groups, etc. in the moieties of $R^1$, $R^{1'}$ and Z of the compounds falling into the extent of claim for patent of the present invention contain a functional group capable of participating in the reaction of producing the objective compound of the present invention to produce side-reactions, it is desirable to protect such functional group with a suitable protective group in advance of producing the objective compound.

In this case, as the protective group for the amino group, use is made of aromatic acyl groups such as phthaloyl, benzoyl, p-nitrobenzoyl, p-chlorobenzoyl, toluoyl, p-tert-butylbenzoyl, phenylacetyl, phenoxyacetyl, naphthoyl, benzenesulfonyl, p-toluenesulfonyl, p-tert-butylbenzenesulfonyl, etc., aliphatic acyl groups such as acetyl, propionyl, valeryl, caprylyl, n-decanoyl, acryloyl, pivaloyl, monochloroacetyl, trifluoroacetyl, methanesulfonyl, camphorsulfonyl, etc., esterified carboxyl groups such as ethoxycarbonyl, tert-butoxycarbonyl, iso-bornyloxycarbonyl, cyclohexyloxycarbonyl, phenyloxycarbonyl, benzyloxycarbonyl, p-nitrobenzyloxycarbonyl, p-methoxybenzyloxycarbonyl, etc., carbamoyl groups such as methylcarbamoyl, phenylcarbamoyl, naphthylcarbamoyl, etc., or similar thiocarbamoyl groups, and silyl groups such as trimethylsilyl and dimethylsilyl, etc. In addition, the protective groups for the amino group other than the above, as described by J. W. Barton in the chapter 2 of the publication edited by McOmie, are also used similarly.

As the protective group for the hydroxyl group, use is made of acyl groups such as formyl, acetyl, monochloroacetyl, trifluoroacetyl, methoxyacetyl, phenoxyacetyl, benzoyl, benzoylformyl, p-nitrobenzoyl, ethoxycarbonyl, 2,2,2-trichloroethoxycarbonyl, 2,2,2-tribromoethoxycarbonyl, benzyloxycarbonyl, p-nitrophenoxycarbonyl, etc., as well as tetrahydropyranyl, tetrahydrothiofuranyl, methoxytetrahydropyranyl, trityl, benzyl, tert-butyl, trimethylsilyl, dimethylsilyl groups, etc. In addition, similarly usable are the protective groups for the alcoholic hydroxyl groups other than the above-mentioned, as described by C. B. Reese in the chapter 3 of the above publication edited by McOmie, and the protective groups for the phenolic hydroxyl groups other than the above-mentioned, as described by E. Haslam in the chapter 4 thereof.

As the protective group for the carboxyl group, use is made for example of methyl, ethyl, tert-butyl, tert-amyl, phenyl, p-nitrophenyl, 2,2,2-trichloroethyl, benzyl, p-methoxybenzyl, p-nitrobenzyl, trityl, benzhydryl, bis(p-methoxyphenyl)methyl, methoxymethyl, ethoxymethyl, benzyloxymethyl, phenacyl, pivaloyloxymethyl, acetoxymethyl, phthalidyl, 2-methylthioethyl, trimethylsilyl, dimethylsilyl, etc. In addition, the protective groups for the carboxyl group other than the above-mentioned, as described by E. Haslam in the chapter 5 of the above publication edited by McOmie are used similarly.

In short, by using these protective groups to protect in advance of the reaction the functional groups capable of participating in the reaction, the protective groups may be left as they are contained after completion of the reaction to thereby produce the final objective compounds of the present invention, or the protective groups may be removed after completion of the reaction to thereby produce the final objective compounds. After all, since type of protective groups, means of introducing them and means of removing them are well known and established techniques in the fields of cephalosporins, penicillins and peptides, such techniques may be employed in the present invention as well.

The cephalosporin derivatives of the present invention, as represented by the general formulas (Ic), (Id) and (IV), and their pharmacologically allowable salts possess excellent antibacterial activities against both gram-positive bacteria (e.g. Staphylococcus aureus, Bacillus subtilis, etc.) and gram-negative bacteria (e.g. Escherichia coli, Proteus vulgaris, Proteus morganii, Klebsiella pneumoniae, etc.) and are low in toxicity, thus being safely employed as the prophylactic or therapeutic agent for infections obserbed in man or animals such as rats (mice•rats), etc., due to these bacteria or as a disinfectant for surgical instruments, sickrooms, etc. These compounds may be combined with a suitable carrier or excipient such as lactose, starch etc., to administer locally as a powder preparation, or may be dissolved or suspended in a liquid for dissolution such as physiological saline solution, etc., to use as a solution or suspension.

The objective compounds of the present invention can be employed in the same manner as known cephalosporin antibiotics such as cephalothin. When the objective compounds of the present invention are used as a disinfectant, it is desirable to use aqueous solutions (of which concentration is about twice the minimal growth inhibitory concentration) of the objective compounds of the present invention.

Examples are described below to illustrate in more detail the contents of the present invention.

In the meanwhile, the symbols to be employed in these Examples, etc. designate the same meanings as those normally employed in the general chemistry. The meanings of the following symbols are clarified below to make sure of them.

DMF: dimethylformamide
AcOEt: Ethyl acetate
MeOH: Methanol
AcOH: Acetic acid
DMSO: Dimethylsulfoxide
s: Singlet d: Doublet
t: Triplet
m: Multiplet
dd: Double doublet
ABq: AB type quartet
br: broad

EXAMPLE 1

Diphenylmethyl 7-(2-thienylacetamido)-2-methyl-3-formyloxymethyl-ceph-2-em-4-carboxylate A 2.5 g portion of zinc powder was added to a solution of 0.7 g of diphenylmethyl 7-(2-thienylacetamido)-2-exomethylene-3-acetoxymethylceph-3-em-4-carboxylate 1-oxide in 30 ml of 90% HCOOH, and then the mixture was stirred at room temperature for 1.5 hours. AcOEt and H$_2$O were added to the reaction solution, and then insolubles were filtered out to separate out the AcOEt layer. The AcOEt layer was washed with saturated aqueous NaHCO$_3$ solution and with saturated aqueous NaCl solution, and then dried over Na$_2$SO$_4$. After distilling off the AcOEt under reduced pressure, the residue was placed on a column of silica gel, and the fractions eluted with benzene.AcOEt (10:1) were collected, followd by distilling off the solvent under reduced pressure, thereby yielding 381 mg (57%) of diphenylmethyl 7-(2-thienylacetamido)-2-methyl-3-formyloxymethylceph-2-em-4-carboxylate.

IR $\nu_{max}^{KBr}$ cm$^{-1}$: 1790, 1735, 1670, 1190.

NMR (DMSO-d$_6$)δ: 2.01 (3H, br.s, 2—CH$_3$), 3.77 (2H,s, —CH$_2$—CO—), 4.67 and 4.90 (1H,ABq,J=13.0 Hz, —CH$_2$—O—, respectively), 5.12(1H,d,J=4.5 Hz,6-H), 5.25(1H,d,J=1.0 Hz,4-H), 5.46(1H,dd,J=4.5, 8.5 Hz,7-H), 6.78 to 7.00(3H,m,thiophene proton (3- and 4-position),—CH(C$_6$H$_5$)$_2$), 7.15 to 7.55(11H,m,thiophene proton (5-position),C$_6$H$_5$x2), 8.02(1H,s,—CHO), 9.14(1H,d,J=8.5 Hz,—CO—NH—).

Elemental analysis, for C$_{29}$H$_{26}$N$_2$O$_6$S$_2$: Calcd.: C 61.90; H 4.66; N 4.98; S 11.40; Found: C 61.79; H 4.56; N 4.87; S 11.30.

EXAMPLE 2

Diphenylmethyl 7-(2-thienylacetamido)-2-methyl-3-hydroxymethyl-ceph-2-em-4-carboxylate A 22.8 ml portion of 2N HCl was added to a solution of 30 g of diphenylmethyl 7-(2-thienylacetamido)-2-methyl-3-formyloxymethylceph-2-em-4-carboxylate in 100 ml of DMF, and the mixture was stirred at room temperature for 20 hours. AcOEt and H$_2$O were added to the reaction solution to separate out the AcOEt layer. The AcOEt layer was washed with 5% aqueous NaHCO$_3$ solution and with saturated aqueous NaCl solution, and dried over Na$_2$SO$_4$, followed by distilling off the AcOEt under reduced pressure. The residue was added on a column of silica gel and washed with CH$_2$Cl$_2$.AcOEt (10:1). Then, the fractions eluted with acetone were collected, and the solvent was distilled off under reduced pressure, resulting 14.6 g (62%) of diphenylmethyl 7-(2-thienylacetamido)-2-methyl-3-hydroxymethylceph-2-em-4-carboxylate.

IR $\nu_{max}^{KBr}$ cm$^{-1}$: 1780, 1745.

NMR (DMSO-D$_6$)δ: 1.95(3H,s,2—CH$_3$), 3.10 to 3.50(1H,br, —CH$_2$—OH), 3.79(2H,s,—CH$_2$—CO—), 3.85 and 4.32(1H,ABq,J=13.0 Hz, —CH$_2$—OH, respectively), 5.06(1H,d,J=4.5 Hz, 6-H), 5.25(1H,s,4-H), 5.44(1H,dd,J=4.5, 8,5 Hz,7-H), 6.70 to 7.10(3H,m,thiophene proton(3- and 4-positions), —CH(C$_6$H$_5$)$_2$), 7.10 to 7.60(11H,m, thiophene proton (5-position), C$_6$H$_5$x2), 9.10(1H,d,J=8.5 Hz, —CO—NH—).

Elemental analysis, for C$_{28}$H$_{26}$N$_2$O$_5$S$_2$: Calcd.: C 62.90; H 4.90; N 5.24; S 11.99; Found: C 62.82; H 4.76; N 5.12; S 11.93.

EXAMPLE 3

Diphenylmethyl 7-(2-thienylacetamido)-2-methyl-3-(1-methyl-1H-tetrazole-5-yl)thiomethylceph-2-em-4-carboxylate A 0.14 ml portion of pyridine was added to a solution of 840 mg of diphenylmethyl 7-(2-thienylacetamido)-2-methyl-3-hydroxymethylceph-2-em-4-carboxylate in 45 ml of CH$_2$Cl$_2$. 0.124 ml of SOCl$_2$ was added at −10° C., followed by stirring at the same temperature for 30 minutes, and then H$_2$O was added to the solution to separate out the CH$_2$Cl$_2$ layer. The CH$_2$Cl$_2$ layer was washed with H$_2$O and with saturated aqueous NaCl solution, and dried over MgSO$_4$ to distill off the CH$_2$Cl$_2$ under reduced pressure. The residue was dissolved in 10 ml of DMF, and 180 mg of 1-methyl-5-mercaptotetrazole was added, followed by stirring overnight. The DMF was distilled off under reduced pressure, and the residue was added on a column of silica gel. The fractions eluted with CH$_2$Cl$_2$.AcOEt (20:1) were collected, and the solvent was distilled off, thus yielding 546 mg (55%) of diphenylmethyl 7-(2-thienylacetamido)-2-methyl-3-(1-methyl-1H-tetrazol-5-yl)thiomethylceph-2-em-4-carboxylate.

IR $\nu_{max}^{KBr}$ cm$^{-1}$: 1780, 1745.

NMR (DMSO-d$_6$)δ: 1.98(3H,s,2—CH$_3$), 3.77(2H,s,—CH$_2$—CO—), 3.84(3H,s,tetrazole, 1—CH$_3$), 4.06 and 4.47(1H,ABq,J=13.0 Hz), —CH$_2$—S—, respectively), 5.11(1H,d,J=4.0 Hz,6-H), 5.41(1H,s, 4-H), 5.48(1H,dd,J=4.0, 7.5 Hz,7-H), 6.80 to 7.00(3H,m, thiophene proton (3- and 4-positions), —CH(C$_6$H$_5$)$_2$), 7.10 to 7.66(11H,m,thiophene proton (5-position), C$_6$H$_5$x2), 9.16(1H,d, J=7.5 Hz, —CO—NH—).

Elemental analysis, for C$_{30}$H$_{28}$N$_6$O$_4$S$_3$: Calcd.: C 56.94; H 4.46; N 13.28; S 15.20; Found: C 56.87; H 4.42; N 13.14; S 14.83.

EXAMPLE 4

Diphenylmethyl 7-(2-thienylacetamido)-2α-methyl-3-(1-methyl-1H-tetrazol-5-yl)thiomethylceph-3-em-4-carboxylate 1-oxide A 217 mg quantity of m-chloroperbenzoic acid was added to a solution of 662 mg of diphenylmethyl 7-(2-thienylacetamido)-2-methyl-3-(1-methyl-1H-tetrazol-5-yl)thiomethylceph-2-em-4-carboxylate in 30 ml of CH$_2$Cl$_2$ at −10° C., and the mixture was stirred at the same temperature for 1 hour. The reaction solution was washed with 10% Na$_2$S$_2$O$_3$ solution and with saturated aqueous NaCl solution, and dried over MgSO$_4$ to distill off the CH$_2$Cl$_2$ under reduced pressure. The residue was added on a column of silica gel, and the fractions eluted with CH$_2$Cl$_2$.AcOEt (5:1) were collected, followed by distilling off the solvent, thus yielding 321 mg (47%) of diphenylmethyl 7-(2-thienylacetamido)-2α-methyl-3-(1-methyl-1H-tetrazol-5-yl)thiomethylceph-3-em-4-carboxylate 1-oxide.

IR $\nu_{max}^{KBr}$ cm$^{-1}$: 1800, 1745, 1690, 1050.

NMR (DMSO-d$_6$)δ: 1.27(3H,d,J=7.5 Hz, 2α—CH$_3$), 3.84(5H,s, tetrazole 1 —CH$_3$ and —CH$_2$—CO—), 4.01(1H,q,J=7.5 Hz,2β-H), 4.25 (2H,s,—CH$_2$—S—), 4.96(1H,d,J=5.0 Hz, 6-H), 5.96(1H,dd,J=5.0, 8.5 Hz,7-H), 6.80 to 7.00(3H,m, thiophene proton (3- and 4-positions), —CH(C<sub>6</sub>H<sub>5</sub>)<sub>2</sub>), 7.10 to 7.70(11H,m,thiophene proton (5-position), $\underline{C_6H_5}$x2), 8.37(1H,d,J=8.5 Hz,—CO—N$\underline{H}$—).

Elemental analysis, for $C_{30}H_{28}N_6O_5S_3$: Calcd.: C 55.54; H 4.35; N 12.96; S 14.83; Found: C 55.59; H 4.36; N 12.98; S 14.31.

EXAMPLE 5

Diphenylmethy 7-(2-thienylacetamido)-2α-methyl-3-(1-methyl-1H-tetrazol-5-yl)thiomethylceph-3-em-4-carboxylate A 0.38 ml portion of PCl<sub>3</sub> was added to a solution of 326 mg of diphenylmethyl 7-(2-thienylacetamido)-2α-methyl-3-(1-methyl-1H-tetrazol-5-yl)thiomethylceph-3-em-4-carboxylate 1-oxide in 5 ml of DMF at −10° C., followed by stirring at the same temperature for 15 minutes. AcOEt and 5% aqueous NaHCO<sub>3</sub> solution were added to the reaction solution to separate out the AcOEt layer. The AcOEt layer was washed with saturated aqueous NaCl solution and dried over Na<sub>2</sub>SO<sub>4</sub>, followed by distilling off the AcOEt under reduced pressure. The residue was added on a column of silica gel, and the fractions eluted with CH<sub>2</sub>Cl<sub>2</sub>.AcOEt (25:1) were collected, followed by distilling off the solvent under reduced pressure, thus yielding 225 mg (71%) of diphenylmethyl 7-(2-thienylacetamido)-2α-methyl-3-(1-methyl-1H-tetrazol-5-yl)thiomethylceph-3-em-4-carboxylate.

IR $\nu_{max}^{KBr}$ cm<sup>−1</sup>: 1790, 1735, 1700.

NMR (DMSO-d<sub>6</sub>)δ: 1.53(3H,d,J=7.0 Hz,2α—C$\underline{H_3}$), 3.74(2H,s, —C$\underline{H_2}$—CO—), 3.84(3H,s,tetrazole1—C$\underline{H_3}$), 4.01(1H,q,J=$\overline{7.0}$ Hz, 2β-$\underline{H}$), 4.18(2H,s,—C$\underline{H_2}$—S—), 5.27(1H,d,J=5.0 Hz,6-$\underline{H}$), $\overline{5.85}$(1H,dd,J=$\overline{5.0}$ and 8.5 Hz,7-$\underline{H}$), 6.80 to 7.00($\overline{3H}$,m,thiophene proton (3- and 4-positions), —CH(C<sub>6</sub>H<sub>5</sub>)<sub>2</sub>), 7.15 to 7.60(11H,m,thiophene proton (5-position), $\underline{C_6H_5}$x2), 9.17(1H,d,J=8.5 Hz,—CO—N$\underline{H}$—).

NOE: When 2α—CH<sub>3</sub> was irradiated, the area of 6-position proton increased by 20%.

Elemental analysis, for $C_{30}H_{28}N_2O_6S_2$: Calcd.: C 62.48; H 4.89; N 4.86; S 11.12; Found: C 62.73; H 4.76; N 4.68; S 11.09.

EXAMPLE 6

Sodium 7-(2-thienylacetamido)-2α-methyl-3-(1-methyl-1H-tetrazol-5-yl)thiomethylceph-3-em-4-carboxylate A solution of 105 mg of diphenylmethyl 7-(2-thienylacetamido)-2α-methyl-3-(1-methyl-1H-tetrazol-5-yl)thiomethylceph-3-em-4-carboxylate in 0.1 ml of anisole and 5 ml of CF<sub>3</sub>—COOH was stirred at room temperature for 20 minutes. After distilling off CF<sub>3</sub>COOH under reduced pressure, the residue was dissolved in AcOEt, and then transferred into 5% aqueous NaHCO<sub>3</sub> solution. The water layer, after being adjusted to pH 7 with 5% H<sub>3</sub>PO<sub>4</sub>, was added on a column of Amberlite XAD-II (produced by Rohm & Haas). The column was washed with water, and the fractions eluted with 10% aqueous MeOH solution were collected, concentrated under reduced pressure and then freeze-dried, thus yielding 72 mg (95%) of sodium 7-(2-thienylacetamido)-2α-methyl-3-(1-methyl-1H-tetrazol-5-yl)thiomehylceph-3-em carboxylate.

TLC [silica gel 60F-254 (produced by Merck), developing solvent: AcOEt.AcOH (10:1)], Rf 0.30.

IR $\nu_{max}^{KBr}$ cm<sup>−1</sup>: 1770, 1685.

NMR (D<sub>2</sub>O)δ: 1.52(3H,d,J=7.5 Hz, 2α—C$\underline{H_3}$), 3.76(1H,q,J=7.5 Hz,2β-$\underline{H}$), 3.86(2H,s,—C$\underline{H_2}$CO—), 3.97(3H,s,tetrazol 1—C$\underline{H_3}$), 4.02 and 4.27(1H,ABq,J=13.5 Hz, —C$\underline{H_2}$—S—, respectively), 5.17 (1H,d,J=5.0 Hz,6-$\underline{H}$), 5.68(1H,d,J=5.0 Hz,7-$\underline{H}$), 6.90 to 7.10(2H, m,thiophene proton (3- and 4-positions)), 7.20 to 7.40(1H,m, thiophene proton (5-position)).

Elemental analysis, for $C_{17}H_{17}N_6O_4S_3Na.3/2H_2O$: Calcd.: C 39.60; H 3.91; N 16.30; S 18.66; Found: C 39.38; H 3.72; N 16.32; S 18.54.

EXAMPLE 7

Diphenylmethyl 7-(2-thienylacetamido)-2,3-diexomethylenecepham-4-carboxylate

A 14 g portion of Zn powder was added to a solution of 4 g of diphenylmethyl 7-(2-thienylacetamido)-2-methylene-3-acetoxymethylceph-3-em-4-carboxylate in 160 ml of AcOH, followed by stirring at room temperature for 45 minutes. AcOEt and H<sub>2</sub>O were added to the reaction solution, and insolubles were filtered out to separate out the AcOEt layer. The AcOEt layer was washed with saturated aqueous NaHCO<sub>3</sub> and with saturated aqueous NaCl solution, and dried over Na<sub>2</sub>SO<sub>4</sub>. After distilling off the AcOEt under reduced pressure, the residue was added on a column of silica gel, and the fractions eluted with benzene.AcOEt (10:1) were collected. The solvent was distilled off under reduced pressure, and Et<sub>2</sub>O was then added to the residue, resulting in 2.3 g (64%) of crystals of diphenylmethyl 7-(2-thienylacetamido)-2,3-di-methylenecepham-4-carboxylate.

m.p. 126° C. (decomp.).

IR $\nu_{max}^{KBr}$ cm<sup>−1</sup>: 1770, 1735, 1660.

NMR (DMSO-d<sub>6</sub>)δ: 3.74(2H,s,—C$\underline{H_2}$—CO—), 5.18(1H,d,J=4.5 Hz, 6-$\underline{H}$), 5.35(1H,s,2-methylene), 5.40(1H,dd,J=4.5, 8.5 Hz,7-$\underline{H}$), 5.51(2H,s,3-methylene), 5.59(1H,s,2-methylene), 6.80 to 7.00 (3H,m,thiophene proton (3- and 4-positions),—CH(C<sub>6</sub>H<sub>5</sub>)<sub>2</sub>), 7.20 to 7.60(11H,m,thiophene proton (5-position), $\underline{C_6H_5}$x2), 9.11(1H, d,J=8.5 Hz,—CO—N$\underline{H}$—).

MS m/e: 516(M+).

Elemental analysis, for $C_{28}H_{24}N_2O_4S_2$: Calcd.: C 65.09; H 4.68; N 5.42; S 12.41; Found: C 65.02; H 4.71; N 5.30; S 12.14.

EXAMPLE 8

By the same procedure as in Example 1, there was obtained diphenylmethyl 7-phenylacetamido-2-methyl-3-formyloxymethylceph-2-em-4-carboxylate from diphenylmethyl 7-phenylacetamido-2-methylene-3-acetoxymethylceph-3-em-4-carboxylate (yield of 63%).

IR $\nu_{max}^{KBr}$ cm<sup>−1</sup>: 1790, 1740.

NMR (DMSO-d<sub>6</sub>)δ: 2.00(3H,br,s,2—C$\underline{H_3}$), 3.53(2H,s,C<sub>6</sub>H<sub>5</sub>—C$\underline{H_2}$—), 4.63 and 4.88(1H,ABq,J=13.0 Hz, —C$\underline{H_2}$—O—, respectively), 5.08(1H, d,J=4.0 Hz,6-$\underline{H}$), 5.24(1H,br,s,4-$\underline{H}$), 5.43(1H,dd,J=4.0,7.5 Hz, 7-$\underline{H}$), 6.79(1H,s,—C$\underline{H}$(C<sub>6</sub>H<sub>5</sub>)<sub>2</sub>), 7.10 to 7.55(15H,m,C<sub>6</sub>H<sub>5</sub>x3), 7.97(1H,s,—C$\underline{H}$O), 9.08(1H,d,J=7.5 Hz, —CO—N$\underline{H}$—).

Elemental analysis, for $C_{30}H_{28}N_2O_5S$: Calcd.: C 68.16; H 5.34; N 5.30; S 6.07; Found: C 68.08; H 5.12; N 5.23; S 6.01.

EXAMPLE 9

By the same procedure as in Example 2, there was obtained diphenylmethyl 7-phenylacetamido-2-methyl-3-hydroxymethylceph-2-em-4-carboxylate from diphenylmethyl 7-phenylacetamido-2-methyl-3-formyloxymethylceph-2-em-4-carboxylate. (Yield of 64%).

IR $\nu_{max}^{KBr}$ cm$^{-1}$: 1790, 1740.

NMR (DMSO-d$_6$)δ: 1.98(3H,s,2—CH$_3$), 3.25(1H,br,s,—OH), 3.52(2H,s,—CH$_2$—CO—), 3.83 and 4.27(1H,ABq,J=13.0 Hz, —CH$_2$—O—, respectively), 5.02(1H,d,J=4.0 Hz,6-H), 5.23(1H,s,4-H), 5.38 (1H,dd,J=4.0, 8.0 Hz,7-H), 6.78(1H,s,—CH(C$_6$H$_5$)$_2$), 7.10 to 7.50 (15H,m,C$_6$H$_5$x3), 9.08(1H,d,J=8.0 Hz, —CO—NH—).

Elemental analysis, for C$_{30}$H$_{28}$N$_2$O$_5$S: Calcd.: C 70.02; H 5.48; N 2.72; S 6.23; Found: C 69.91; H 5.23; N 2.52; S 6.40.

EXAMPLE 10

By the same procedure as in Example 3, there was obtained diphenylmethyl 7-phenylacetamido-2-methyl-3-(1-methyl-1H-tetrazol-5-yl)thiomethylceph-2-em-4-carboxylate from diphenylmethyl 7-phenylacetamido-2-methyl-3-hydroxymethylceph-2-em-4-carboxylate (Yield of 59%).

IR $\nu_{max}^{KBr}$ cm$^{-1}$: 1790, 1750.

NMR (DMSO-d$_6$)δ: 1.97(3H,br,s,2—CH$_3$), 3.53(2H,s,—CH$_2$—CO—), 3.83(3H,s,tetrazole 1—CH$_3$), 4.03 and 4.45(1H,ABq,J=13.0 Hz, —CH$_2$—S—, respectively), 5.07(1H,d,J=4.0 Hz,6-H), 5.40(1H,br,s, 4-H), 5.44(1H,dd,J=4.0, 7.5 Hz,7-H), 6.83(1H,s,—CH(C$_6$H$_5$)$_2$), 7.10 to 7.50(15H,m,C$_6$H$_5$x3), 9.11(1H,d,J=7.5 Hz, —CONH—).

Elemental analysis, for C$_{32}$H$_{30}$N$_6$O$_4$S$_2$: Calcd.: C 61.32; H 4.82; N 13.41; S 10.23; Found: C 61.05; H 4.82; N 13.64; S 10.51.

EXAMPLE 11

By the same procedure as in Example 4, there was obtained diphenylmethyl 7-phenylacetamido-2α-methyl-3-(1-methyl-1H-tetrazol-5-yl)thiomethylceph-3-em-4-carboxylate from diphenylmethyl 7-phenylacetamido-2-methyl-3-(1-methyl-1H-tetrazol-5-yl)thiomethylceph-2-em-4-carboxylate (Yield of 50%).

IR $\nu_{max}^{KBr}$ cm$^{-1}$: 1800, 1740.

NMR (DMSO-d$_6$)δ: 1.27(3H,d,J=7.0 Hz, 2α—CH$_3$), 3.62(2H,s, —CHH$_2$—CO—), 3.84(3H,s,tetrazole 1—CH$_3$), 4.00(1H,q,J=7.0 Hz,2β-H), 4.23(2H,br,s,—CH$_2$—S—), 4.94(1H,d,J=5.0 Hz,6-H), 5.94(1H,dd, J=5.0, 8.5 Hz,7-H), 6.91(1H,s,—CH(C$_6$H$_5$)$_2$), 7.10 to 7.60(15H,m, C$_6$H$_5$x3), 8.31(1H,d,J=8.5 Hz, —CO—NH—).

Elemental analysis, for C$_{32}$H$_{30}$N$_6$O$_5$S$_2$: Calcd.: C 59.79; H 4.70; N 13.08; S 9.98; Found: C 59.81; H 4.76; N 13.07; S 10.01.

EXAMPLE 12

By the same procedure as in Example 5, there was obtained diphenylmethyl 7-phenylacetamido-2α-methyl-3-(1-methyl-1H-tetrazol-5-yl)thiomethylceph-3-em-4-carboxylate from diphenylmethyl 7-phenylacetamido-2α-methyl-3-(1-methyl-1H-tetrazol-5-yl)thiomethylceph-3-em-4-carboxylate 1-oxide (Yield of 71%).

IR $\nu_{max}^{KBr}$ cm$^{-1}$: 1790, 1730.

NMR (DMSO-d$_6$)δ: 1.52(3H,d,J=7.0 Hz,2α—CH$_3$), 3.50(2H,s, —CH$_2$—CO—), 3.83(3H,s,tetrazole 1—CH$_3$), 4.00(1H,q,J=7.0 Hz, 2β-H), 4.17(2H,s,—CH$_2$—S—), 5.23(1H,d,J=5.0 Hz, 6-H), 5.83(1H, dd,J=5.0, 8.5 Hz,7-H), 6.88(1H,s,—CH(C$_6$H$_5$)$_2$), 7.10 to 7.60 (15H,m,C$_6$H$_5$x3), 9.12(1H,d,J=8.5 Hz, —CO—NH—).

Elemental analysis, for C$_{32}$H$_{30}$N$_6$O$_4$S$_2$: Calcd.: C 61.32; H 4.82; N 13.41; S 10.23; Found: C 61.15; H 4.77; N 13.13; S 10.09.

EXAMPLE 13

By the same procedure as in Example 6, there was obtained sodium 7-phenylacetamido-2α-methyl-3-(1-methyl-1H-tetrazol-5-yl)thiomethylceph-3-em-4-carboxylate from diphenylmethyl 7-phenylacetamido-2α-methyl-3-(1-methyl-1H tetrazol-5-yl)thiomethylceph-3-em-4-carboxylate (Yield of 71%).

IR $\nu_{max}^{KBr}$ cm$^{-1}$: 1770, 1680.

NMR (D$_2$O)δ: 1.62(3H,d,J=7.0 Hz, 2α—CH$_3$), 3.77(2H,s,—CH$_2$—CO—), 3.87(1H,q,J=7.0 Hz,2β-H), 4.08(3H,s,tetrazole 1—CH$_3$), 4.17 and 4.35(1H,ABq,J=13.0 Hz,—CH$_2$—S—, respectively), 5.28 (1H,d,J=5.0 Hz,6-H), 5.78(1H,d,J=5.0 Hz,7-H), 7.45(5H,s,C$_6$H$_5$—).

Elemental analysis, for C$_{19}$H$_{19}$O$_4$N$_6$S$_2$Na.2H$_2$O: Calcd.: C 44.00; H 4.47; N 16.21; S 12.37; Found: C 44.07; H 4.37; N 15.95; S 12.19.

EXAMPLE 14

Diphenylmethyl 7-amino-2α-methyl-3-(1-methyl-1H-tetrazol-5-yl)thiomethylceph-3-em-4-carboxylate A 3.7 ml portion of pyridine was added to a solution of diphenylmethyl 7-(2-thienylacetamido)-2α-methyl-3-(1-methyl-1H-tetrazol-5-yl)thiomethylceph-3-em-4-carboxylate in 100 ml of CH$_2$Cl$_2$, followed by adding 2.4 g of PCl$_5$ at −12° C., further followed by stirring at the same temperature for 45 minutes. MeOH was added in once, and the mixture was further stirred at −10° C. for 30 minutes and at room temperature for 1 hour. 100 ml of 0.5M K$_2$HPO$_4$ solution was added to the reaction solution, followed by adding further 25% H$_3$PO$_4$ to adjust to pH 1.5. After stirring for 45 minutes, the CH$_2$Cl$_2$ layer was separated out, then washed with saturated aqueous NaCl solution, and dried over MgSO$_4$ to distill off the CH$_2$Cl$_2$ under reduced pressure. Et$_2$O was added to the residue, thus yielding 1.73 g (72%) of crystals of 7-amino-2α-methyl-3-(1-methyl-1H-tetrazol-5-yl)thiomethylceph-3-em-4-carboxylate.

m.p. 158° C. (decomp.).

IR $\nu_{max}^{KBr}$ cm$^{-1}$: 1780, 1735.

NMR (DMSO-d$_6$+D$_2$O)δ: 1.56(3H,d,J=7.0 Hz, 2α—CH$_3$), 3.82 (3H,s,tetrazole 1—CH$_3$), 3.93(1H,q,J=7.0 Hz, 2β-H), 4.16(2H,s, —CH$_2$—S—), 4.90(1H,d,J=5.0 Hz,6-H), 5.11(1H,d,J=5.0 Hz,7-H), 6.84(1H,s,—CH(C$_6$H$_5$)$_2$), 7.10 to 7.60(10H,m,C$_6$H$_5$x2).

Elemental analysis, for C$_{24}$H$_{24}$N$_6$O$_3$S$_2$: Calcd.: C 56.67; H 4.76; N 16.53; S 12.61; Found: C 56.61; H 4.68; N 16.46; S 12.40.

EXAMPLE 15

By the same procedure as in the above-mentioned Example, there was obtained diphenylmethyl 7-amino-2α-methyl-3-(1-methyl-1H-tetrazol-5-yl)thiomethylceph-3-em-4-carboxylate from diphenylmethyl 7-phenylacetamido-2α-methyl-3-(1-methyl-1H-tetrazol-5-yl)thiomethylceph-3-em-4-carboxylate (Yield of 69%). The thus obtained product showed the m.p., IR and NMR in complete agreement with those of the product obtained in the above-mentioned Example.

EXAMPLE 16

Diphenylmethyl 7-[D(−)-α-(t-butoxycarboxamido)-α-(2-thienyl)acetamido]-2α-methyl-3-(1-methyl-1H-tetrazol-5-yl)thiomethylceph-3-em-4-carboxylate A 180 mg quantity of dicyclohexyl carbodiimide was added to a solution of 224 mg of D(−)-t-butoxycarboxamido-α-2-thienylacetic acid and 400 mg of diphenylmethyl 7-amino-2α-methyl-3-(1-methyl-1H-tetrazol-5-yl)thiomethylceph-3-em-4-carboxylate in 50 ml of $CH_2Cl_2$ at −10° C., and the mixture was then stirred at the same temperature for 1 hour and then at room temperature for 2 hours. The resultant dicyclohexyl urea was filtered out, and the filtrate was washed with 5% $H_3PO_4$, 5% aqueous $NaHCO_3$ solution and saturated aqueous NaCl solution, and dried over $MgSO_4$, followed by distilling off $CH_2Cl_2$ under reduced pressure. The residue was added on a column of silica gel, and the fractions eluted with $CH_2Cl_2$. AcOEt (10:1) were collected to distill off the solvent under reduced pressure, resulting in 560 mg (95%) of diphenylmethyl 7-[D(−)-α-(t-butoxycarboxamido)-α-(2-thienyl)acetamido]-2α-methyl-3-(1-methyl-1H-tetrazol-5-yl)thiomethylceph-3-em-4-carboxylate.

IR $v_{max}^{KBr}$ cm$^{-1}$: 1800, 1730, 1705, 1180.

NMR (DMSO-d$_6$)δ: 1.40(9H,s,—C(C$\underline{H}_3$)$_3$), 1.56(3H,d,J=7.0 Hz, 2α—C$\underline{H}_3$), 3.83(3H,s,tetrazole 1—C$\underline{H}_3$), 3.96(1H,q,J=7.0 Hz,2β-$\underline{H}$), 4.16(2H,s,—C$\underline{H}_2$—S—), 5.24(1H,d,J=5.0 Hz,6-$\underline{H}$), 5.50(1H,d,J=8.0 Hz, >C$\underline{H}$—CO—), 5.89(1H,dd,J=5.0, 8.5 Hz,7-$\underline{H}$), 6.80 to 7.10(3H,m,thiophene proton (3- and 4-positions), —C$\underline{H}$(C$_6$H$_5$)$_2$), 7.10 to 7.60(12H, m,thiophene proton (5-position), C$_6$$\underline{H}_5$x2, >CH—N$\underline{H}$—CO—), 9.25(1H,d, J=8.5 Hz, —CON$\underline{H}$—).

Elemental analysis, for C$_{35}$H$_{37}$N$_7$O$_6$S$_3$: Calcd.: C 56.21; H 4.99; N 13.11; S 12.86; Found: C 56.34; H 5.17; N 13.01; S 12.69.

EXAMPLE 17

7-[D(−)-α-amino-α-(2-thienyl)acetamide]-2α-methyl-3-(1-methyl-1H-tetrazol-5-yl)thiomethylceph-3-em-4-carboxylic acid A solution of 500 mg of diphenylmethyl 7-[D(−)-α-(t-butoxycarboxamido)-α-(2-thienyl)acetamido]-2α-methyl-3-(1-methyl-1H-tetrazol-5-yl)thiomethylceph-3-em-4-carboxylate in 0.55 ml of anisole and 20 ml of CF$_3$COOH was stirred at room temperature for 20 minutes. After distilling off the CF$_3$COOH under reduced pressure, the residue was distributed in AcOEt and H$_2$O to separate out the water layer. The water layer was adjusted to pH 4.5 with 5% aqueous NaHCO$_3$ solution, and added on a column of Amberlite XAD-II (produced by Rohm & Haas). After washing the column with water, the fractions eluted with 30% aqueous MeOH were collected, concentrated under reduced pressure and freeze-dried, thus yielding 156 mg (49%) of 7-[D(−)-α-amino-α-(2-thienyl)acetamido]-2α-methyl-3-(1-methyl-1H-tetrazol-5-yl)thiomethylceph-3-em-4-carboxylic acid.

IR $v_{max}^{KBr}$ cm$^{-1}$: 1785, 1700, 1605.

NMR (DMSO-d$_6$+D$_2$O)δ: 1.49(3H,d,J=7.0 Hz,2α—C$\underline{H}_3$), 3.80(3H, s,tetrazole 1—C$\underline{H}_3$), 3.88(2H,s,—C$\underline{H}_2$—S—), 4.20(1H,q,J=7.0 Hz,2β-$\underline{H}$), 5.08(1H,d,J=5.0 Hz,6-H), 5.22(1H,s,>C$\underline{H}$—CO—), 5.63(1H,d,J=5.0 Hz, 7-$\underline{H}$), 6.85 to 7.30(2H,m,thiophene proton(3- and 4-positions)), 7.35 to 7.60(1H,m,thiophene proton (5-position)).

Elemental analysis, for C$_{17}$H$_{19}$N$_7$O$_4$S$_3$.3/2H$_2$O: Calcd.: C 40.14; H 4.36; N 19.28; S 18.91; Found: C 40.10; H 4.64; N 19.28; S 18.63.

EXAMPLE 18

7-[D(−)-α-(4-ethyl-2,3-dioxo-1-piperazinecarboxamido)-α-(2-thienyl)acetamido]-2α-methyl-3-(1-methyl-1H-tetrazol-5-yl)thiomethylceph-3-em-4-carboxylic acid Five % aqueous NaHCO$_3$ was added to a solution of 160 mg of 7-[D(−)-α-amino-α-(2-thienyl)acetamido]-2α-methyl-3-(1-methyl-1H-tetrazol-5-yl)thiomethylceph-3-em-4-carboxylic acid in 10 ml of H$_2$O and 10 ml of tetrahydrofuran to adjust to pH 8.0. 68 mg of 4-ethyl-2,3-dioxo-1-piperazinylcarbonyl chloride was added to the solution at 0° C. and, after stirring at the same temperature for 30 minutes, AcOEt was added to the reaction solution to separate out the water layer. 5% H$_3$PO$_4$ was then added to the water layer to adjust to pH 2.0 so as to extract with AcOEt. The AcOEt layer was washed with H$_2$O and saturated aqueous NaCl solution, and dried over Na$_2$SO$_4$, followed by distilling off the AcOEt, thus yielding 102 mg (47%) of crystals of 7-[D(−)-α-(4-ethyl-2,3-dioxopiperazinecarboxamido)-α-(2-thienyl)acetamido]-2α-methyl-3-(1-methyl-1H-tetrazol-5-yl)thiomethylceph-3-em-4-carboxylic acid.

m.p. 152° C. (decomp.).

IR $v_{max}^{KBr}$ cm$^{-1}$: 1785, 1710, 1690.

NMR (DMSO-d$_6$)δ: 1.09(3H,t,J=7.0 Hz, —CH$_2$—C$\underline{H}_3$), 1.50(3H,d,J=7.0 Hz,2α—C$\underline{H}_3$), 3.39(2H,q,J=7.0 Hz, —C$\underline{H}_2$—CH$_3$), 3.40 to 4.00 (5H,m,piperazinylmethylene (5- and 6-positions), 2β-$\underline{H}$), 3.90(3H, s,tetrazole 1—C$\underline{H}_3$), 4.08 and 4.34(1H,ABq,J=13.0 Hz, —C$\underline{H}_2$—S—, respectively), 5.16(1H,d,J=5.0 Hz,6-$\underline{H}$), 5.79(1H,dd,J=5.0, 9.0 Hz, 7-$\underline{H}$), 5.85(1H,d,J=7.0 Hz, >C$\underline{H}$—NH—), 6.80 to 7.20(2H,m,thiophene proton(3- and 4-positions)), 7.30 to 7.55(1H,m,thiophene proton (5-position)), 9.50(1H,d,J=9.0 Hz, —CO—N$\underline{H}$—), 9.75(1H,d,J=7.0 Hz, >CH—N$\underline{H}$—).

Elemental analysis, for C$_{24}$H$_{27}$N$_9$O$_7$S$_3$: Calcd.: C 44.36; H 4.19; N 19.40; S 14.80; Found: C 44.21; H 4.18; N 19.23; S 14.75.

EXAMPLE 19

By the same procedure as in Example 16, there was obtained diphenylmethyl 7-[D(−)-α-(t-butoxycarboxamido)-α-(phenyl)acetamido]-2α-methyl-3-(1-methyl-1H-tetrazol-5-yl)thiomethylceph-3-em-4-carboxylate from D(−)-α-t-butoxycarboxamide-α-phenylacetic acid and diphenylmethyl 7-amino-2α-methyl-3-(1-methyl-1H-tetrazol-5-yl)thiomethylceph-3-em-4-carboxylate (Yield of 96%).

IR $v_{max}^{KBr}$ cm$^{-1}$: 1800, 1730, 1700.

NMR (DMSO-d$_6$)δ: 1.37(9H,s, —C(C$\underline{H}_3$)$_3$), 1.47(3H,d,J=7.0 Hz, 2α—C$\underline{H}_3$), 3.83(3H,s,tetrazole 1—C$\underline{H}_3$), 3.92(1H,q,J=7.0 Hz,2β-$\underline{H}$), 4.15(2H,s,C$\underline{H}_2$—S—), 5.18(1H,d,J=4.5 Hz,6-$\underline{H}$), 5.30(1H,d,J=8.5 Hz, >C$\underline{H}$—CO—), 5.88(1H,dd,J=4.5,8.5 Hz,7-$\underline{H}$), 6.89(1H,s,—C$\underline{H}$(C$_6$H$_5$)$_2$), 7.10 to 7.60(16H,m,C$_6$$\underline{H}_5$x3, and —NHCOOC(CH$_3$)$_3$), 9.18(1H,d,J=8.5 Hz, —CON$\underline{H}$—).

Elemental analysis, for $C_{37}H_{39}N_7O_6S_2$: Calcd.: C 59.90; H 5.30; H 13.22; S 8.64; Found: C 60.09; H 5.68; N 13.08; S 8.63.

EXAMPLE 20

By the same procedure as in Example 17, there was obtained 7-[D(−)-α-amino-α-(phenyl)acetamido]-2α-methyl-3-(1-methyl-1H-tetrazol-5-yl)thiomethylceph-3-em-4-carboxylic acid from diphenylmethyl 7-[D(−)-α-(t-butoxycarboxamido)-α-(phenyl)acetamido]-2α-methyl-3-(1-methyl-1H-tetrazol-5-yl)thiomethylceph-3-em-4-carboxylate (Yield of 19%).

IR $\nu_{max}^{KBr}$ cm$^{-1}$: 1765, 1695.

NMR (CD$_3$COOD)δ: 1.56(3H,d,J=7.0 Hz,2α—CH$_3$), 3.88(1H,q,J=7.0 Hz,2β-H), 3.92(3H,s,tetrazole1—CH$_3$), 4.1 and 4.54(1H, ABq,J=13.0 Hz,—CH$_2$—S—, respectively), 5.10(1H,d,J=5.0 Hz,6-H), 5.40(1H,s, >CH—CO—), 5.89(1H,d,J=5.0 Hz,7-H), 7.35 to 7.65 (5H,m,C$_6$H$_5$—).

Elemental analysis, for $C_{19}H_{21}N_7O_4S_2 \cdot H_2O$: Calcd.: C 46.23; H 4.70; N 19.87; S 12.99; Found: C 46.17; H 4.66; N 19.60; S 12.79.

EXAMPLE 21

Diphenylmethyl 7-(2-thienylacetamido)-2-methyl-3-acetoxymethylceph-2-em-4-carboxylate A solution of 4.4 g of NaBH$_4$ in 250 ml of EtOH was added to a solution of 45 g of diphenylmethyl 7-(2-thienylacetamido)-2-methylene-3-acetoxymethylceph-3-em-4-carboxylate in 150 ml of tetrahydrofuran at 0° C., and the mixture was stirred for 7 minutes, followed by adding 15 ml of AcOH. After distilling off the solvent under reduced pressure, AcOEt and H$_2$O were added to the residue to separate out the AcOEt layer. The AcOEt layer was washed with 5% aqueous NaHCO$_3$ and saturated aqueous sodium chloride solution, and dried over Na$_2$SO$_4$ to distill off the AcOEt under reduced pressure. The residue was added on a column of silica gel, and the fractions eluted with CH$_2$Cl$_2$.AcOEt (10:1) were collected, followed by distilling off the solvent under reduced pressure, yielding 18.7 g (41%) of diphenylmethyl 7-(2-thienylacetamido)-2-methyl-3-acetoxymethylceph-2-em-4-carboxylate.

IR $\nu_{max}^{KBr}$ cm$^{-1}$: 1770, 1730, 1650.

NMR (DMSO-d$_6$)δ: 1.78(3H,s,—CO—CH$_3$), 1.96(3H,s,2—CH$_3$), 3.72(2H,s,—CH$_2$—CO—), 4.57 and 4.73(1H,ABq,J=13.0 Hz, —CH$_2$—O—, respectively), 5.06(1H,d,J=4.5 Hz,6-H), 5.20(1H,s,4-H), 5.42(1H,dd,J=4.5,8.5 Hz,7-H), 6.70 to 6.95(3H,m,thiophene proton (3- and 4-positions), —CH(C$_6$H$_5$)$_2$), 7.15 to 7.50(11H,m,thiophene proton(5-position), C$_6$H$_5$x2), 9.12(1H,d,J=8.5 Hz, —CO—NH—).

Elemental analysis, for $C_{30}H_{28}N_2O_6S_2$: Calcd.: C 62.48; H 4.80; N 4.86; S 11.12; Found: C 62.55; H 4.89; N 4.97; S 11.03.

EXAMPLE 22

Diphenylmethyl 7-(2-thienylacetamido)-2-methyl-3-acetoxymethylceph-3-em-4-carboxylate 1-oxide A solution of 13.7 g of m-chloroperbenzoic acid in 50 ml of CH$_2$Cl$_2$ was added to a solution of 37.3 g of diphenylmethyl 7-(2-thienylacetamido)-2-methyl-3-acetoxymethylceph-2-em-4-carboxylate in 300 ml of CH$_2$Cl$_2$ at −20° C., and the mixture was stirred at the same temperature for 30 minutes. The reaction solution was washed with 5% aqueous NaHCO$_3$ and saturated aqueous NaCl solutions, and dried over MgSO$_4$, followed by distilling off the solvent under reduced pressure. AcOEt.Et$_2$O (1:3) was added to the residue, thus yielding 32 g (84%) of crystals of diphenylmethyl 7-(2-thienylacetamido)-2-methyl-3-acetoxymethylceph-3-em-4-carboxylate 1-oxide.

Elemental analysis, for $C_{30}H_{28}N_2O_7S_2$: Calcd.: C 60.79; H 4.76; N 4.73; S 10.82; Found: C 60.83; H 4.86; N 4.61; S 10.63.

EXAMPLE 23

Diphenylmethyl 7-(2-thienylacetamido)-2β-methyl-3-acetoxymethyl-ceph-3-em-4-carboxylate and diphenylmethyl 7-(2-thienylacetamido)-2α-methyl-3-acetoxymethyl-ceph-3-em-4-carboxylate A 41.5 ml portion of PCl$_3$ was added to a solution of 32 g of diphenylmethyl 7-(2-thienylacetamido)-2-methyl-3-acetoxymethylceph-3-em-4-carboxylate 1-oxide in 200 ml of DMF at −50° C., and the mixture was stirred at −30° C. for 5 minutes and poured in ice water to extract with AcOEt. The AcOEt layer was washed with 5% aqueous NaHCO$_3$ and saturated aqueous sodium chloride solutions, and dried over Na$_2$SO$_4$, followed by distilling off the AcOET under reduced pressure, thus yielding crude crystals. Recrystalization from AcOEt-Et$_2$O (1:3) afforded 17 g (55%) of diphenylmethyl 7-(2-thienylacetamido)-2β-methyl-3-acetoxymethylceph-3-em-4-carboxylate.

m.p. 152° C. (decomp.).

TLC [Silica gel 60F-254 (produced by Merck), developing solvent: toluene.AcOEt (5:1) Rf 0.26.

IR $\nu_{max}^{KBr}$ cm$^{-1}$: 1795, 1740, 1680, 1230.

NMR (DMSO-d$_6$)δ: 1.45(3H,d,J=7.0 Hz,2β—CH$_3$), 1.95(3H,s,—CO—CH$_3$), 3.79(2H,s,—CH$_2$—CO—), 4.04(1H,q,J=7.0 Hz,2α-H), 4.57 and 4.99(1H,ABq,J=13.0 Hz, —CH$_2$—O—, respectively), 5.31(1H,d,J=5.0 Hz,6-H), 5.77(1H,dd,J=5.0,8.0 Hz,7-H), 6.90 to 7.05(3H,m,thiophene proton (3- and 4-positions), —CH(C$_6$H$_5$)$_2$), 7.20 to 7.60(11H,m,thiophene proton (5-position), C$_6$H$_5$x2), 9.12(1H,d,J=8.0 Hz, —CO—NH—).

NOE: when 2β-CH$_3$ was irradiated, the area of 6-position proton did not increase.

Elemental analysis, for $C_{30}H_{28}N_2O_6S_2$: Calcd.: C 62.48; H 4.89; N 4.86; S 11.12; Found: C 62.35; H 4.71; N 4.80; S 11.21.

After concentrating the mother liquor, the residue was added on a column of silica gel, and eluted with toluene. AcOEt (15:1). The fractions foremost eluted were collected, and the solvent was distilled off under reduced pressure, thus yielding 0.3 g (1%) of diphenylmethyl 7-(2-thienylacetamido)-2α-methyl-3-acetoxymethylceph-3-em-4-carboxylate.

TLC [Silica gel 60F-254 (produced by Merck), developing solvent: toluene.AcOEt (5:1)] Rf 0.30.

IR $\nu_{max}^{KBr}$ cm$^{-1}$: 1795, 1740, 1700, 1230.

NMR (DMSO-d$_6$)δ: 1.47(3H,d,J=7.0 Hz,2α—CH$_3$), 1.91(3H,s, —CO—CH$_3$), 3.75(2H,s,—CH$_2$—CO—), 3.84(1H,q,J=7.0 Hz,2β-H), 4.51 and 4.82(1H,ABq,J=13.0 Hz,—CH$_2$—O—, respectively), 5.24 (1H,d,J=5.0 Hz,6-H), 5.82(1H,dd,J=5.0,8.0 Hz,7-H), 6.80 to 7.00(3H,m,thiophene proton (3- and 4-positions), —CH(C$_6$H$_5$)$_2$), 7.10 to 7.50(11H,m,thiophene proton (5-position),C$_6$H$_5$x2), 9.13(1H,d,J=8.0 Hz,—CO—NH—).

NOE: when 2α—CH₃ was irradiated, the area of 6-position proton increased by 32%.

Elemental analysis, for $C_{30}H_{28}N_2O_6S_2$: Calcd.: C 62.48; H 4.89; N 4.86; S 11.12; Found: C 62.73; H 4.74; N 4.68; S 11.09.

EXAMPLE 24

Sodium 7-(2-thienylacetamido)-2β-methyl-3-acetoxymethyl-ceph-3-em-4-carboxylate

A solution of 1.4 g of diphenylmethyl 7-(2-thienylacetamido)-2β-methyl-3-acetoxymethylceph-3-em-4-carboxylate in 3 ml of anisole and 20 ml of CF₃COOH was stirred at room temperature for 15 minutes. After distilling off CF₃COOH under reduced pressure, the residue was dissolved in AcOEt, and then transferred into 5% aqueous NaHCO₃. The water layer was adjusted to pH 2.0 with 5% H₃PO₄ to extract again with AcOEt. The AcOEt layer was washed with saturated aqueous NaCl solution, and dried over Na₂SO₄, and the AcOEt was distilled off under reduced pressure, thus yielding crude crystals of 7-(2-thienylacetamido)-2β-methyl-3-acetoxymethylceph-3-em-4-carboxylic acid. The crude crystals were dissolved in 5% aqueous NaHCO₃, adjusted to pH 7.0 with addition of 5% H₃PO₄ and then added on a column of Amberlite XAD-II (produced by Rohm & Hass). The fractions eluted with H₂O were collected, concentrated under reduced pressure and freeze-dried, thus yielding 829 mg (79%) of sodium 7-(2-thienylacetamido)-2β-methyl-3-acetoxymethylceph-3-em-4-carboxylate.

IR $\nu_{max}^{KBr}$ cm⁻¹: 1760, 1735, 1655, 1600.

NMR (D₂O)δ: 1.46(3H,d,J=7.0 Hz,2β—$\underline{CH_3}$), 2.11(3H,s,—CO—$\underline{CH_3}$), 3.91(2H,s,—$\underline{CH_2}$—CO—), 3.98(1H,q,J=7.0 Hz,2α-$\underline{H}$), 4.69 and 5.07 (1H,ABq,J=13.0 Hz,—$\underline{CH_2}$—O—, respectively), 5.21(1H,d,J=5.0 Hz,6-$\underline{H}$), 5.60(1H,d,J=5.0 Hz,7-$\underline{H}$), 6.95 to 7.10(2H,m,thiophene proton (3- and 4-positions)), 7.30 to 7.55(1H,m,thiophene proton(5-position)).

Elemental analysis, for $C_{17}H_{17}N_2O_6S_2Na.3/2H_2O$: Calcd.: C 44.44; H 4.39; N 6.10; S 13.96; Found: C 44.62; H 4.11; N 5.85; S 13.75.

EXAMPLE 25

By the same procedure as in the above-mentioned Example, there was obtained sodium 7-(2-thienylacetamido)-2α-methyl-3-acetoxymethylceph-3-em-4-carboxylate from diphenylmethyl 7-(2-thienylacetamido)-2α-methyl-3-acetoxymethylceph-3-em-4-carboxylate (Yield of 66%).

IR $\nu_{max}^{KBr}$ cm⁻¹: 1780, 1680, 1240.

NMR (D₂O)δ: 1.63(3H,d,J=7.5 Hz,2α—$\underline{CH_3}$), 2.33(3H,s,—CO—$\underline{CH_3}$), 3.70(1H,q,J=7.5 Hz,2β-$\underline{H}$), 4.00(2H,s,—$\underline{CH_2}$—CO—), 4.78 and 5.00(1H,ABq,J=13.0 Hz,—$\underline{CH_2}$—O—, respectively), 5.30(1H,d,J=5.0 Hz,6-$\underline{H}$), 5.82(1H,d,J=5.0 Hz,7-$\underline{H}$), 7.07 to 7.23(2H,m,thiophene proton (3- and 4-positions)), 7.40 to 7.58(1H,m,thiophene proton (5-position)).

Elemental analysis, for $C_{17}H_{17}N_2O_6S_2.3/2H_2O$: Calcd.: C 44.44; H 4.39; N 6.10; S 13.96; Found: C 44.81; H 4.48; N 6.04; S 13.76.

EXAMPLE 26

Sodium 7-(2-thienylacetamido)-2β-methyl-3-(1-methyl-1-H-tetrazol-5-yl)thiomethylceph-3-em-4-carboxylate In 20 ml of 1/15M phosphoric acid buffer solution (pH 6.4) were dissolved 410 mg of 7-(2-thienylacetamido)-2β-methyl-3-acetoxymethylceph-3-em-4-carboxylic acid and 84 mg of NaHCO₃, and 139 mg of 1-methyl-5-mercaptotetrazole was then added to the solution. The reaction solution was stirred at 50° C. for 6 hours, while maintaining it at pH 6.4 by pouring 5% aqueous NaHCO₃, and then added on a column of Amberlite XAD-II (produced by Rohm & Haas), followed by washing with water and eluting by the gradient method with 0 to 70% aqueous methanol. The eluted fractions were collected, concentrated under reduced pressure and freeze-dried, thus yielding 148 mg (30%) of sodium 7-(2-thienylacetamido)-2β-methyl-3-(1-methyl-1H-tetrazol-5-yl)thiomethylceph-3-em-4-carboxylate.

TLC [Silica gel 60F-254 (produced by Merck), developing solvent: AcOEt.AcOH (10:1)] Rf 0.23.

IR $\nu_{max}^{KBr}$ cm⁻¹: 1760, 1670, 1600.

NMR (D₂O)δ: 1.48(3H,d,J=7.0 Hz,2β—$\underline{CH_3}$), 3.89(2H,s,—$\underline{CH_2}$—CO—), 3.95(1H,q,J=7.0 Hz,2α-$\underline{H}$), 4.03(3H,s,tetrazole 1—$\underline{CH_3}$), 4.43 and 4.87(1H,ABq,J=13.0 Hz,—$\underline{CH_2}$—S—, respectively), 5.11 (1H,d,J=4.5 Hz,6-$\underline{H}$), 5.47(1H,d,J=4.5 Hz,7-$\underline{H}$), 6.90 to 7.10 (2H,m,thiophene proton (3- and 4-positions)), 7.25 to 7.45(1H,m,thiophene proton (5-position)).

Elemental analysis, for $C_{17}H_{17}N_6O_4S_3Na.3/2H_2O$: Calcd.: C 39.60; H 3.91; N 16.30; S 18.66; Found: C 39.80; H 3.84; N 16.20; S 18.53.

EXAMPLE 27

By the same procedure as in the above-mentioned Example, there was obtained sodium 7-(2-thienylacetamido)-2β-methyl-3-(5-methyl-1,3,4-thiadiazol-2-yl)thiomethylceph-3-em-4-carboxylate from 7-(2-thienylacetamido)-2β-methyl-3-acetoxymethylceph-3-em-4-carboxylic acid and 5-methyl-2-mercapto-1,3,4-thiadiazole (Yield of 42%).

TLC [Silica gel 60F-254 (produced by Merck), developing solvent: AcOEt.AcOH (10:1)] Rf 0.33.

IR $\nu_{max}^{KBr}$ cm⁻¹: 1760, 1675, 1605.

NMR (D₂O)δ: 1.44(3H,d,J=7.0 Hz,2β—$\underline{CH_3}$), 2.73(3H,s,thiadiazol 5—$\underline{CH_3}$), 3.89(2H,s,—$\underline{CH_2}$—CO—), 4.09(1H,q,J=7.0 Hz,2α-$\underline{H}$), 3.87 and 4.71(1H,ABq,J=14.0 Hz,—$\underline{CH_2}$—S—, respectively), 5.10 (1H,d,J=4.5 Hz,6-$\underline{H}$), 5.50(1H,d,J=4.5 Hz,7-$\underline{H}$), 6.96 to 7.10(2H,m,thiophene proton (3- and 4-positions)), 7.25 to 7.50(1H,m,thiophene proton(5-position)).

Elemental analysis, for $C_{18}H_{17}N_4O_4S_4Na.H_2O$: Calcd.: C 41.29; H 3.66; N 10.70; S 24.49; Found: C 41.27; H 3.51; N 10.98; S 24.47.

EXAMPLE 28

By the same procedure as in Example 26, there was obtained 7-(2-thienylacetamido)-2β-methyl-3-(1-carboxymethyl-1H-tetrazol-5-yl)thiomethylceph-3-em-4-carboxylic acid disodium salt from 7-(2-thienylacetamido)-2β-methyl-3-acetoxymethylceph-3-em-4-carboxylic acid and 1-carboxymethyl-5-mercaptotetrazole (Yield of 20%).

IR $\nu_{max}^{KBr}$ cm$^{-1}$: 1770, 1670, 1620.

NMR (D$_2$O)δ: 1.48(3H,d,J=7.0 Hz,2β—C$\underline{H}_3$), 3.92(2H,s,—C$\underline{H}_2$—CO—), 3.97 and 4.74(1H,ABq,J=13.0 Hz,—C$\underline{H}_2$—S—, respectively), 4.07(1H,q,J=7.0 Hz,2α-H), 5.03(2H,s,tetrazole 1—C$\underline{H}_2$—CO—), 5.16 (1H,d,J=4.5 Hz,6-H), 5.52(1H,d,J=4.5 Hz,7-H), 7.00 to 7.20(2H,m,thiophene proton (3- and 4-positions)), 7.30 to 7.50(1H,m,thiophene proton(5-position)).

Elemental analysis, for C$_{18}$H$_{16}$N$_6$O$_6$S$_3$Na$_2$.3H$_2$O: Calcd.: C 35.52; H 3.64; N 13.81; S 15.80; Found: C 35.92; H 3.62; N 13.30; S 15.88.

EXAMPLE 29

Diphenylmethyl 7-amino-2β-methyl-3-acetoxymethylceph-3-em-4-carboxylate

A 6.8 ml portion of pyridine was added to a solution of 4 g of diphenylmethyl 7-(2-thienylacetamido)-2β-methyl-3-acetoxymethylceph-3-em-4-carboxylate in 170 ml of CH$_2$Cl$_2$, and 4.35 g of PCl$_5$ was then added to the mixture at −12° C., followed by stirring at the same temperature for 45 minutes. 45 ml of MeOH was added in once to the mixture, followed by stirring at −10° C. for 30 minutes and further at room temperature for 1 hour. 100 ml of 0.5M K$_2$HPO$_4$ solution and further 25% H$_3$PO$_4$ were added to the reaction solution to adjust to pH 1.5, followed by stirring for 45 minutes and separating out the CH$_2$Cl$_2$ layer. The layer was washed with saturated aqueous NaCl solution and dried over MgSO$_4$, and the CH$_2$Cl$_2$ was distilled off under reduced pressure. The residue was added on a column of silica gel, and the fractions eluted with CH$_2$Cl$_2$.AcOEt (10:1) were collected to distill off the solvent under reduced pressure. Petroleum ether was added to the residue, thus yielding 3.7 g (87%) of crystals of diphenylmethyl 7-amino-2β-methyl-3-acetoxymethylceph-3-em-4-carboxylate, m.p. 101° C. (decomp.).

IR $\nu_{max}^{KBr}$ cm$^{-1}$: 1760, 1730, 1220.

NMR (DMSO-d$_6$+D$_2$O)δ: 1.40(3H,d,J=7.0 Hz,2β—C$\underline{H}_3$), 1.89(3H,s,—CO—C$\underline{H}_3$), 3.94(1H,q,J=7.0 Hz,2α-H), 4.48 and 4.98(1H,ABq,J=13.0 Hz,—C$\underline{H}_2$—O—, respectively), 4.76(1H,d,J=7.0 Hz,6-H), 5.12 (1H,d,J=5.0 Hz,7-H), 6.85(1H,s,—C$\underline{H}$(C$_6$H$_5$)$_2$), 7.33(10H,s,C$_6$H$_5$x2).

Elemental analysis, for C$_{24}$H$_{24}$N$_2$O$_5$S: Calcd.: C 63.70; H 5.35; N 6.19; S 7.08; Found: C 63.62; H 5.25; N 6.11; S 7.03.

EXAMPLE 30

Diphenylmethyl 7-[2-(2-chloroacetylaminothiazol-4-yl)-(Z)-2-methoxyiminoacetamido]-2β-methyl-3-acetoxymethylceph-3-em-4-carboxylate A 0.5 ml portion of Et$_3$N, along with 1.13 g of 2-(2-chloroacetylaminothiazol-4-yl)-(Z)-2-methoxyiminoacetyl chloride, was added to a solution of 1.6 g of diphenylmethyl 7-amino-2β-methyl-3-acetoxymethylceph-3-em-4-carboxylate in 50 ml of CH$_2$Cl$_2$ at −40° C., and the mixture was stirred at from −20° C. to −15° C. for 45 minutes. The reaction solution was washed with H$_2$O, 5% aqueous NaHCO$_3$ and saturated aqueous NaCl solutions, and dried over MgSO$_4$, followed by distilling off the CH$_2$Cl$_2$ under reduced pressure. The residue was added on a column of silica gel, and the fractions eluted with CH$_2$Cl$_2$.AcOEt (5:1) were collected to distill off the solvent, thus yielding 1.5 g (61%) of diphenylmethyl 7-[2-(2-chloroacetylaminothiazol-4-yl)-(Z)-2-methoxyiminoacetamido]-2β-methyl-3-acetoxymethylceph-3-em-4-carboxylate.

Beilstein reaction: positive

IR $\nu_{max}^{KBr}$ cm$^{-1}$: 1790, 1740, 1685, 1230.

EXAMPLE 31

Sodium 7-[2-(2-aminothiazol-4-yl)-(Z)-2-methoxyiminoacetamido]-2β-methyl-3-acetoxymethylceph-3-em-4-carboxylate A solution of 1.45 g of diphenylmethyl 7-[2-(2-chloroacetylaminothiazol-4-yl)-(Z)-2-methoxyiminoacetamido]-2β-methyl-3-acetoxymethylceph-3-em-4-carboxylate in 2 ml of anisole and 25 ml of CF$_3$COOH was stirred at room temperature for 20 minutes. After distilling off the CF$_3$COOH under reduced pressure, the residue was distributed in AcOEt and 5% aqueous NaHCO$_3$, and the water layer was then separated out. The water layer was adjusted to pH 6.8 with 5% H$_3$PO$_4$, added with 0.36 g of thiourea and stirred overnight. The mixture was then added on a column of Amberlite XAD-II (produced by Rohm & Haas), followed by washing the column with water to elute by the gradient procedure with 0 to 70% aqueous MeOH. The fractions eluted were collected, concentrated under reduced pressure and freeze-dried, thus yielding 295 mg (30%) of sodium 7-[2-(2-aminothiazol-4-yl)-(Z)-2-methoxyiminoacetamido]-2β-methyl-3-acetoxymethylceph-3-em-4-carboxylate.

IR $\nu_{max}^{KBr}$ cm$^{-1}$: 1770, 1670, 1610, 1240.

NMR (D$_2$O)δ: 1.50(3H,d,J=7.0 Hz,2β—C$\underline{H}_3$), 2.10(3H,s,—CO—C$\underline{H}_3$), 4.00(3H,s,—O—C$\underline{H}_3$), 4.05(1H,q,J=7.0 Hz,2α-H), 4.69 and 5.07(1H,ABq,J=13.0 Hz,—C$\underline{H}_2$—O—, respectively), 5.34(1H,d,J=4.5 Hz,6-H), 5.78(1H,d,J=4.5 Hz,7-H), 7.03(1H,s,thiazole 5-H).

Elemental analysis, for C$_{17}$H$_{18}$N$_5$O$_7$S$_2$Na.2H$_2$O: Calcd.: C 38.70; H 4.02; N 13.28; S 12.16; Found: C 38.61; H 4.32; N 13.21; S 12.06.

EXAMPLE 32

By the same procedure as in Example 26, there was obtained sodium 7-[2-(2-aminothiazol)-4-yl)-(Z)-2-methoxyiminoacetamido]-2β-methyl-3-(1-methyl-1H-tetrazol-5-yl)thiomethylceph-3-em-4-carboxylate from sodium 7-[2-(2-aminothiazol-4-yl)-(Z)-2-methoxyiminoacetamido]-2β-methyl-3-acetoxymethylceph-3-em-4-carboxylate and 1-methyl-5-mercaptotetrazole (Yield of 32%).

IR $\nu_{max}^{KBr}$ cm$^{-1}$: 1770, 1680, 1615.

NMR (D$_2$O)δ: 1.53(3H,d,J=7.0 Hz,2β—C$\underline{H}_3$), 4.00(3H,s,tetrazole 1-C$\underline{H}_3$), 4.06(3H,s,—O—C$\underline{H}_3$), 4.17(1H,q,J=7.0 Hz,2α-H), 5.26(d,J=4.5 Hz,6-H), 5.68(d,J=4.5 Hz,7-H), 7.05(1H,s,thiazole,5-H).

Elemental analysis, for C$_{17}$H$_{18}$N$_9$O$_5$S$_3$Na.2H$_2$O: Calcd.: C 34.98; H 3.80; N 21.60; S 16.48; Found: C 34.83; H 3.75; N 21.53; S 16.32.

EXAMPLE 33

(1) Production of starting compounds

D(−)-α-(4-ethyl-2,3-dioxo-1-piperazinecarboxyamido)-α-2-thienylacetic acid

To a suspension of 2 g of D(−)-α-thienylglycine in 40 ml of CH$_2$Cl$_2$ was added 3.4 ml of trimethylchlorosilane, and 3.6 ml of Et$_3$N was then added dropwise to the mixture at from 0° to 5° C. After increasing the temperature gradually, the mixture was stirred at room temperature for 1.5 hours and added with 3 g of 4-ethyl-2,3-dioxo-1-piperazinecarbonyl chloride, followed by stirring for 2 hours. 45 ml of H$_2$O was added to the reaction mixture, followed by stirring for 45 minutes to separate out the CH$_2$Cl$_2$ layer. The CH$_2$Cl$_2$ layer was extracted with saturated aqueous NaHCO$_3$ solution to separate out the water layer. The water layer was adjusted to pH 2.0 with 25% H$_3$PO$_4$ and extracted again with CH$_2$Cl$_2$. The CH$_2$Cl$_2$ layer was washed with saturated aqueous NaCl solution, and dried over MgSO$_4$, followed by distilling off the CH$_2$Cl$_2$ under reduced pressure. Et$_2$O was added to the residue, resulting in 2.6 g (63%) of D(−)-α-(4-ethyl-2,3-dioxo-1-piperazinecarboxamido)-2-thienylacetic acid.

IR $\nu_{max}^{KBr}$ cm$^{-1}$: 1740, 1730, 1675.

(2) Sodium 7-[D(−)-α-(4-ethyl-2,3-dioxo-1-piperazinecarboxamido)-α-(2-thienyl)acetamido]-2β-methyl-3-acetoxymethylceph-3-em-4-carboxylate A 250 mg quantity of dicyclohexylcarbodiimide was added to a solution of 358 mg of D(−)-α-(4-ethyl-2,3-dioxo-1-piperazinylcarboxamido)-2-thienylacetic acid and 500 mg of diphenylmethyl 7-amino-2β-methyl-3-acetoxymethylceph-3-em-4-carboxylate in 50 ml of CH$_2$Cl$_2$ at −10° C., and the mixture was stirred at the same temperature for 1 hour and then at room temperature overnight. The resultant dicyclohexyl urea was filtered out, and the filtrate was washed with 5% H$_3$PO$_4$, 5% aqueous NaHCO$_3$ and saturated aqueous NaCl solution, successively, and dried over MgSO$_4$, followed by distilling off the CH$_2$Cl$_2$ under reduced pressure. The residue was dissolved in 1 ml of anisole and 20 ml of CF$_3$COOH, and the mixture was stirred at room temperature for 20 minutes, followed by distilling off the CF$_3$COOH under reduced pressure. The residue was dissolved in AcOEt and then transferred into 5% aqueous NaHCO$_3$. The water layer was adjusted to pH 7.0 with 5% H$_3$PO$_4$, and then added on a column of Amberlite XAD-II (produced by Rohm & Haas), followed by washing the column with water to elute by the gradient method with 0 to 70% aqueous MeOH. The fractions eluted were collected, concentrated under reduced pressure and freeze-dried, thus yielding 140 mg (21%) of sodium 7-[D(−)-α-(4-ethyl-2,3-dioxo-1-piperazinecarboxamido)-α-(2-thienyl)acetamido]-2β-methyl-3-acetoxymethylceph-3-em-4-carboxylate.

IR $\nu_{max}^{KBr}$ cm$^{-1}$: 1760, 1705, 1680, 1600.

NMR (D$_2$O)δ: 1.30(3H,t,J=7.0 Hz, —CH$_2$—CH$_3$), 1.48(3H,d,J=7.0 Hz,2β—CH$_3$), 2.20(3H,s,—CO—CH$_3$), 3.65 to 4.30(5H,m,piperazinemethylene (5-position and 6-position), cephem 2α-H), 4.78 and 5.13 (1H,ABq,J=13.0 Hz,—CH$_2$—O—, respectively), 5.27 (1H,d,J=4.5 Hz,6-H), 5.75(1H,d,J=4.5 Hz,7-H), 5.90(1H,s,>CH—CO—), 7.10 to 7.45(2H,m,thiophene proton (3- and 4-positions)), 7.50 to 7.70(1H,m,thiophene proton (5-position)).

Elemental analysis, for C$_{24}$H$_{26}$N$_5$O$_9$S$_2$Na.H$_2$O: Calcd.: C 45.49; H 4.45; N 11.05; S 10.12; Found: C 45.41; H 4.49; N 11.12; S 10.01.

EXAMPLE 34

7-[D(−)-α-(4-ethyl-2,3-dioxo-1-piperazinecarboxamido)-α-(2-thienyl)acetamido]-2β-methyl-3-(1-methyl-1H-tetrazol-5-yl)thiomethylceph-3-em-4-carboxylic acid A solution of 306 mg of sodium 7-[D(−)-α-(4-ethyl-2,3-dioxo-1-piperazinecarboxamido)-α-(2-thienyl)acetamido]-2β-methyl-3-acetoxymethylceph-3-em-4-carboxylate and 70 mg of 1-methyl-5-mercaptotetrazole in 20 ml of 1/15M phosphoric acid buffer solution (pH 6.4) was stirred at 50° C. for 3 hours, while maintaining it at pH 6.4 by pouring 5% aqueous NaHCO$_3$ solution, and added on a column of Amberlite XAD-II (produced by Rohm & Haas), followed by washing the column with water to elute by the gradient method with 0 to 70% aqueous MeOH. The fractions eluted were collected, concentrated under reduced pressure, adjusted to pH 2.0 with 5% H$_3$PO$_4$ and extracted with AcOEt. The AcOEt layer was washed with H$_2$O and saturated aqueous NaCl solution, successively, and dried over Na$_2$SO$_4$, followed by distilling off the AcOEt under reduced pressure, thus yielding 110 mg (34%) of 7-[D(−)-α-(4-ethyl-2,3-dioxo-1-piperazinecarboxamido)-α-(2-thienyl)acetamido]-2β-methyl-3-(1-methyl-1H-tetrazol-5-yl)thiomethylceph-3-em-4-carboxylic acid.

IR $\nu_{max}^{KBr}$ cm$^{-1}$: 1775, 1680.

NMR (DMSO-d$_6$)δ: 1.09(3H,t,J=7.0 Hz,—CH$_2$—CH$_3$), 1.42(3H,d,J=7.0 Hz,2β—CH$_3$), 3.39(2H,q,J=7.0 Hz,—CH$_2$—CH$_3$), 3.40 to 3.90 (5H,m,piperazinemethylene 5- and6-positions, 2α-H), 3.92 (3H,s,tetrazole, 1—CH$_3$), 4.08 and 4.75(1H,ABq,J=13.0 Hz,—CH$_2$—S—, respectively), 5.10(1H,d,J=5.0 Hz,6-H), 5.63(1H,dd,J=5.0, 9.0 Hz, 7-H), 5.90(1H,d,J=7.0 Hz,>CH—NH—), 6.80 to 7.20(2H,m,thiophene proton (3- and 4-positions)), 7.30 to 7.55(1H,m,thiophene proton(5-position)), 9.43(1H,d,J=9.0 Hz, —CO—NH—), 9.74(1H,d,J=7.0 Hz,>CH—NH—).

Elemental analysis, for C$_{24}$H$_{27}$N$_9$O$_7$S$_3$: Calcd.: C 44.36; H 4.19; N 19.40; S 14.80; Found: C 44.32; H 4.08; N 19.35; S 14.65.

EXAMPLE 35

(1) Production of a starting compound

D(−)-α-(2,3-dioxo-4-ethyl-1-piperazinecarboxamido)-1,4-cyclohexadienylacetic acid A 2.04 ml portion of trimethylchlorosilane was added to a solution of 1.2 g of D(−)-α-amino-1,4-cyclohexadienylacetic acid in 50 ml of CH$_2$Cl$_2$, and the mixture was maintained at a temperature of 0° to 5° C. to add dropwise 2.16 ml of Et$_3$N. After increasing the temperature gradually, the mixture was stirred at room temperature for 1.5 hours, and 1.8 g of 2,3-dioxo-4-ethyl-1-piperazinecarbonyl chloride was added, followed by stirring for 2 hours. Then, 45 ml of H$_2$O was added to the reaction mixture, which was stirred for 45 minutes to separate out the CH$_2$Cl$_2$ layer. The CH$_2$Cl$_2$ layer was extracted with saturated aqueous NaHCO$_3$ to separate out the water layer. The water layer was adjusted to pH 2.0 with 25% H$_3$PO$_4$, and extracted again with CH$_2$Cl$_2$. The CH$_2$Cl$_2$ layer was washed with saturated aqueous NaCl solution, and dried over MgSO$_4$, followed by distilling off the CH$_2$Cl$_2$ under reduced pressure. The residue was treated with petroleum ether, thus yielding 1.9 g (75%) of D(−)-α-(2,3-dioxo-4-ethyl-1-piperazinecarboxamido)-1,4-cyclohexadienylacetic acid.

(2) Sodium 7-[D(−)-α-(4-ethyl-2,3-dioxo-1-piperazinecarboxamido)-α-(1,4-cyclohexadienyl)acetamido]-2β-methyl-3-acetoxymethylceph-3-em-4-carboxylate A 226 mg quantity of dicyclohexylcarbodiimide was added to a solution of 321 mg of D(−)-α-(4-ethyl-2,3-dioxo-1-piperazinecarboxamido)-1,4-cyclohexadienylacetic acid and 452 mg of diphenylmethyl 7-amino-2β-methyl-3-acetoxymethylceph-3-em-4-carboxylate in 50 ml of $CH_2Cl_2$ at −10° C., and the mixture was stirred at the same temperature for 1 hour and then at room temperature overnight. The resultant dicyclohexyl urea was filtered out, and the filtrate was washed with 5% $H_3PO_4$, 5% aqueous $NaHCO_3$ and saturated aqueous NaCl solution, successively, and dried over $MgSO_4$, followed by distilling off the $CH_2Cl_2$ under reduced pressure. The residue was dissolved in 1 ml of anisole and 20 ml of $CF_3COOH$, and then stirred at room temperature for 20 minutes. After distilling off the $CF_3COOH$ under reduced pressure, the residue was dissolved in AcOEt and then transferred into 5% aqueous $NaHCO_3$ solution. The water layer was adjusted to pH 7.0 with 5% $H_3PO_4$, and then added on a column of Amberlite XAD-II (produced by Rohm & Haas), followed by washing the column with water to elute by the gradient method with 0 to 70% aqueous MeOH. The fractions eluted were collected, concentrated under reduced pressure and freeze-dried, thus yielding 235 mg (40%) of sodium 7-[D(−)-α-(4-ethyl-2,3-dioxo-1-piperazinecarboxamido)-α-(1,4-cyclohexadienyl)acetamido]-2β-methyl-3-acetoxymethylceph-3-em-4-carboxylate.

IR $\nu_{max}^{KBr}$ cm$^{-1}$: 1775, 1715, 1690, 1620.

NMR ($D_2O$)δ: 1.30 (3H, t, J=7.0 Hz, —$CH_2$—$CH_3$), 1.55(3H, d, J=7.0 Hz, 2β—$CH_3$), 2.20(3H, s, —CO—$CH_3$), 2.82(4H, s, cyclohexadienemethylene (3-position and 6-position), 3.62(2H, q, J=7.0 Hz, —$CH_2$—$CH_3$), 3.65 to 4.30(5H, m, piperazinemethylene(5-position and 6-position), cephem-2α-$\underline{H}$), 4.08 and 5.13(1H, ABq, J=13.0 Hz, —$CH_2$—O—, respectively), 5.07(1H, s, >CH—CO—), 5.33(1H, d, J=4.5 Hz, 6-$\underline{H}$), 5.75(1H, d, J=7.5 Hz, 7-$\underline{H}$), 5.85(2H, s, cyclohexadiene proton (4-position and 5-position)), 6.13(1H, br, s, cyclohexadiene proton (2-position)).

Elemental analysis, for $C_{26}H_{30}N_5O_9SNa.H_2O$: Calcd.: C 49.60; H 5.12; N 11.12; S 5.09; Found: C 49.47; H 5.26; N 11.21; S 5.01.

EXAMPLE 36

Diphenylmethyl 7-(2-thienylacetamido)-2-methyl-3-formylceph-2-em-4-carboxylate

To 250 ml of $CH_2Cl_2$ containing 6.7 ml of pyridine at 20° C. was added 4.2 g of $CrO_3$, and after stirring for 1 hour, a solution of 2.6 g of diphenylmethyl 7-(2-thienylacetamido)-2-methyl-3-hydroxymethylceph-2-em-4-carboxylate in 30 ml of $CH_2Cl_2$ was added to the mixture, followed by stirring vigorously for 5 minutes. 100 ml of 1M citric acid solution was added to the reaction solution, followed by stirring to separate out the $CH_2Cl_2$ layer. The $CH_2Cl_2$ layer was washed with $H_2O$ and saturated aqueous NaCl solution, successively, and dried over $MgSO_4$, followed by distilling off the $CH_2Cl_2$ under reduced pressure. The residue was added on a column of silica gel, and the fractions eluted with $CH_2Cl_2$.ACOEt (20:1) were collected to distill off the solvent under reduced pressure, thus yielding 938 mg (36.2%) of diphenylmethyl 7-(2-thienylacetamido)-2-methyl-3-formylceph-2-em-4-carboxylate.

IR $\nu_{mas}^{KBr}$ cm$^{-1}$: 1790, 1750.

NMR (DMSO-$d_6$)δ: 2.50(3H, s, 2—$CH_3$), 3.78(2H, s, —$CH_2$—CO—), 5.07(1H, d, J=4.5 Hz, 6-$\underline{H}$), 5.45(1H, s, 4-$\underline{H}$), 5.47(1H, dd, J=4.5 Hz, 8.0 Hz, 7-$\underline{H}$), 6.70 to 7.00(3H, m, thiophene proton 3- and 4-positions, —$CH(C_6H_5)_2$), 7.10 to 7.50(11H, m, thiophene proton 5-position, $C_6H_5$x2), 9.16(1H, d, J=8.0 Hz, —CON$\underline{H}$—), 9.99(1H, s, —CHO).

Elemental analysis, for $C_{28}H_{29}N_2O_5S_2$: Calcd.: C 63.14; H 4.54; N 5.26; S 12.04; Found: C 63.01; H 4.29; N 5.12; S 11.98.

EXAMPLE 37

Diphenylmethyl 7-(2-thienylacetamido)-2α-methyl-3-formylceph-3-em-4-carboxylate 1-oxide A solution of 2.5 g of diphenylmethyl 7-(2-thienylacetamido)-2-methyl-3-formylceph-2-em-4-carboxylate and 0.95 g of m-chloroperbenzoic acid in 50 ml of $CH_2Cl_2$ was stirred at room temperature for 1 hour. The reaction solution was washed with 5% aqueous $NaHCO_3$ and saturated aqueous NaCl solution, successively, and dried over $MgSO_4$, followed by distilling off $CH_2Cl_2$ under reduced pressure, thus yielding crude crystals. Recrystallization from $CH_2Cl_2$-AcOEt afforded 1.27 g (50%) of crystals of diphenylmethyl 7-(2-thienylacetamido)-2α-methyl-3-formylceph-3-em-4-carboxylate 1-oxide.

m.p. 168° C. (decomp.).

IR $\nu_{max}^{KBr}$ cm$^{-1}$: 1805, 1725, 1665, 1040.

NMR (DMSO-$d_6$)δ: 1.11(3H, d, J=7.5 Hz, 2α—$CH_3$), 3.89(2H, s, —$CH_2$—CO—), 4.11(1H, q, J=7.5 Hz, 2β-$\underline{H}$), 5.08(1H, d, J=5.0 Hz, 6-$\underline{H}$), 6.20(1H, dd, J=5.0, 8.5 Hz, 7-$\underline{H}$), 6.84 to 7.20(3H, m, thiophene proton (3- and 4-positions), —$CH(C_6H_5)_2$), 7.20 to 7.60(11H, m, thiophene proton (5-position), $C_6H_5$x2), 8.67(1H, d, J=8.5 Hz, —CON$\underline{H}$—), 9.96(1H, s, —CHO).

Elemental analysis, for $C_{28}H_{24}N_2O_6S_2$: Calcd.: C 61.30; H 4.41; N 5.11; S 11.69; Found: C 61.19; H 4.43; N 5.14; S 11.53.

EXAMPLE 38

Diphenylmethyl 7-(2-thienylacetamido)-2α-methyl-3-methoxyiminomethylceph-3-em-4-carboxylate 1-oxide A solution of 133 mg of m-chloroperbenzoic acid in 15 ml of $CH_2Cl_2$ was added to a solution of 392 mg of diphenylmethyl 7-(2-thienylacetamido)-2-methyl-3-methoxyiminomethylceph-2-em-4-carboxylate in 30 ml of $CH_2Cl_2$ at −20° C., and the mixture was stirred at the same temperature for 30 minutes and further at room temperature for 30 minutes. The reaction solution was washed with 5% aqueous $NaHCO_3$ and saturated aqueous NaCl solution, and dried over $MgSO_4$, followed by distilling off the $CH_2Cl_2$ under reduced pressure. The residue was added on a column of silica gel, and the fractions eluted with benzene.AcOEt (10:1) were collected. After distilling off the solvent under reduced pressure, the residue was treated with AcOEt, yielding 252 mg (62%) of crystals of diphenylmethyl 7-(2- thienylacetamido)-2α-methyl-3-methoxyiminomethyl-ceph-3-em-4-carboxylate 1-oxide.

m.p. 203° C. (decomp.).

IR $\nu_{max}^{KBr}$ cm$^{-1}$: 1800, 1730, 1670.

NMR (CDCl$_3$)δ: 1.25(3H, d, J=7.5 Hz, 2α—CH$_3$), 3.84(2H, s, —CH$_2$—CO—), 3.88(3H, s, —OCH$_3$), 4.50(1H, q, J=7.5 Hz, 2β-H), 4.51(1H, d, J=5.0 Hz, 6-H), 6.14(1H, dd, J=5.0, 9.0 Hz, 7-H), 6.80 to 7.05(3H, m, thiophene proton (3- and 4-positions), —CH(C$_6$H$_5$)$_2$), 7.10 to 7.60(12H, m, thiophene proton (5-position), C$_6$H$_5$x2, —CONH—), 8.41 (1H, s, —CHO).

Elemental analysis, for C$_{29}$H$_{27}$N$_3$O$_6$S$_2$: Calcd.: C 60.29; H 4.71; N 7.27; S 11.10; Found: C 60.17; H 4.70; N 7.09; S 10.91.

EXAMPLE 39

Diphenylmethyl 7-(2-thienylacetamido)-2α-methyl-3-methoxyiminomethylceph-3-em-4-carboxylate A 0.3 ml portion of PCl$_3$ was added to a solution of 249 mg of diphenylmethyl 7-(2-thienylacetamido)-2α-methyl-3-methoxyiminomethylceph-3-em-4-carboxylate 1-oxide in 8 ml of DMF at −20° C., and the mixture was stirred at the same temperature for 45 minutes. AcOEt and H$_2$O were added to the reaction solution to separate out the AcOEt layer. The AcOEt layer was washed with 5% aqueous NaHCO$_3$ and saturated aqueous NaCl solution, successively, and dried over Na$_2$SO$_4$, followed by distilling off the AcOEt under reduced pressure. The residue was added on a column of silica gel, and the fractions eluted with benzene.AcOEt (15:1) were collected. After distilling off the solvent under reduced pressure, the residue was treated with Et$_2$O, thus yielding 219 mg (90%) of crystals of diphenylmethyl 7-(2-thienylacetamido)-2α-methyl-3-methoxyiminomethylceph-3-em-4-carboxylate.

m.p. 160° C. (decomp.).

IR $\nu_{max}^{KBr}$ cm$^{-1}$: 1790, 1725, 1665.

NMR (DMSO-d$_6$)δ: 1.50(3H, d, J=7.5 Hz, 2α—CH$_3$), 3.74(2H, s, —CH$_2$—CO—), 3.82(3H, s, —OCH$_3$), 4.35(1H, q, J=7.5 Hz, 2β-H), 5.37 (1H, d, J=4.5 Hz, 6-H), 5.88(1H, dd, J=4.5, 8.5 Hz, 7-H), 6.75 to 7.05(3H, m, thiophene proton 3- and 4-positions, —CH(C$_6$H$_5$)$_2$), 7.10 to 7.60(11H, m, thiophene proton (5-position), C$_6$H$_5$x2), 7.90(1H, s, —CH=N—), 9.18(1H, d, J=8.5 Hz, —CONH—).

NOE: when 2α-CH$_3$ was irradiated, the area of 6-position proton increased by 21%.

Elemental analysis, for C$_{29}$H$_{27}$N$_3$O$_5$S$_2$: Calcd.: C 62.01; H 4.75; N 7.47; S 11.42; Found: C 61.88; H 4.75; N 7.34; S 11.37.

EXAMPLE 40

Sodium 7-(2-thienylacetamido)-2α-methyl-3-methoxyiminomethylceph-3-em-4-carboxylate A solution of 160 mg of diphenylmethyl 7-(2-thienylacetamido)-2α-methyl-3-methoxyiminomethylceph-3-em-4-carboxylate in 0.2 ml of anisole and 6 ml of CF$_3$COOH was stirred at room temperature for 20 minutes. After distilling off the CF$_3$COOH under reduced pressure, the residue was dissolved in AcOEt and then transferred into 5% aqueous NaHCO$_3$. The water layer was adjusted to pH 7.0 with 5% H$_3$PO$_4$, and added on a column of Amberlite XAD-II (produced by Rohm & Haas). After washing the column with water, the fractions eluted with 20% aqueous MeOH were collected, concentrated under reduced pressure and freeze-dried, thus yielding 54 mg (45%) of sodium 7-(2-thienylacetamido)-2α-methyl-3-methoxyiminomethylceph-3-em-4-carboxylate.

IR $\nu_{max}^{KBr}$ cm$^{-1}$: 1775, 1680.

NMR (D$_2$O)δ: 1.56(3H, d, J=7.0 Hz, 2α—CH$_3$), 3.91(5H, s, —OCH$_3$ and —CH$_2$—CO—), 4.22(1H, q, J=7.0 Hz, 2β-H), 5.35(1H, d, J=5.0 Hz, 6-H), 5.78(1H, d, J=5.0 Hz, 7-H), 6.95 to 7.2(2H, m, thiophene proton (3- and 4-positions)), 7.25 to 7.50(1H, m, thiopene proton(5-position)).

Elemental analysis, for C$_{16}$H$_{16}$N$_3$O$_5$S$_2$Na.3/2H$_2$O: Calcd.: C 43.24; H 4.31; N 9.46; S 14.43; Found: C 43.22; H 4.28; N 9.38; S 14.25.

EXAMPLE 41

By the same procedure as in Example 36, there was obtained diphenylmethyl 7-(2-thienylacetamido)-2α-methyl-3-morpholinoethoxyiminomethylceph-3-em-4-carboxylate 1-oxide from diphenylmethyl 7-(2-thienylacetamido)-2α-methyl-3-formylceph-3-em-4-carboxylate 1-oxide and morpholinoethoxyamine hydrochloride (Yield of 52%).

m.p. 167° C. (decomp.).

IR $\nu_{max}^{KBr}$ cm$^{-1}$: 1800, 1730, 1675, 1040.

NMR (DMSO-d$_6$)δ: 1.24(3H, d, J=7.0 Hz, 2α—CH$_3$), 2.20 to 2.60 (4H, m, morpholine methylene 3- and 5-positions), 2.56(2H, t, J=5.5 Hz, —CH$_2$CH$_2$N<), 3.40 to 3.70(4H, m, morpholine methylene (2- and 6-positions)), 3.86(2H, s, —CH$_2$—CO—), 4.16(2H, t, J=5.5 Hz, —OCH$_2$CH$_2$—), 4.43(1H, q, J=7.0 Hz, 2β-H), 5.05(1H, d, J=5.0 Hz, 6-H), 6.02(1H, dd, J=5.0, 8.5 Hz, 7-H), 6.80 to 7.00(3H, m, thiophene proton(3- and 4-positions), —CH(C$_6$H$_5$)$_2$), 7.15 to 7.60(11H, m, thiophene proton(5-position), C$_6$H$_5$x2), 8.14(1H, s, —CH=N—), 8.52(1H, d, J=8.5 Hz, —CO—NH—).

Elemental analysis, for C$_{34}$H$_{36}$N$_4$O$_7$S$_2$: Calcd.: C 60.34; H 5.36; N 8.28; S 9.47; Found: C 60.58; H 5.31; N 8.04; S 9.51.

EXAMPLE 42

By the same procedure as in Example 37, there was obtained diphenylmethy 7-(2-thienylacetamido)-2α-methyl-3-morpholinoethoxyiminomethylceph-3-em-4-carboxylate from diphenylmethyl 7-(2-thienylacetamido)-2α-methyl-3-morpholinoethoxyiminomethylceph-3-em-4-carboxylate 1-oxide (Yield of 86%).

IR $\nu_{max}^{KBr}$ cm$^{-1}$: 1800, 1740, 1705.

NMR (DMSO-d$_6$)δ: 1.52(3H, d, J=7.0 Hz, 2α—CH$_3$), 2.20 to 2.60 (4H, m, morpholine methylene(3- and 5-positions)), 2.56(2H, t, J=5.5 Hz, —CH$_2$CH$_2$N<), 3.40 to 3.68(4H, m, morpholine methylene (2- and 6-positions)), 3.76(2H, s, —CH$_2$—CO—), 4.16(2H, t, J=5.5 Hz, —OCH$_2$CH$_2$—), 4.36(1H, q, J=7.0 Hz, 2β-H), 5.36(1H, d, J=5.0 Hz, 6-H), 5.89(1H, dd, J=5.0, 8.0 Hz, 7-H), 6.85 to 7.00(3H, m, thiophene proton(3- and 4-positions), —CH(C$_6$H$_5$)$_2$), 7.10 to 7.60(11H, m, thiophene proton(5-position), C$_6$H$_5$x2), 7.92(1H, s, —CH=N—), 9.19(1H, d, J=8.0 Hz, —CO—NH—).

Elemental analysis, for C$_{34}$H$_{36}$N$_4$O$_6$S$_2$: Calcd.: C 61.80; H 5.48; N 8.48; S 9.70; Found: C 61.72; H 5.31; N 8.37; S 9.65.

EXAMPLE 43

By the same procedure as in Example 40, there was obtained sodium 7-(2-thienylacetamido)-2α-methyl-3-morpholinoethoxyiminomethylceph-3-em-4-carboxylate from diphenylmethyl 7-(2-thienylacetamido)-2α-methyl-3-morpholinoethoxyiminomethylceph-3-em-4-carboxylate (Yield of 49%).

IR $\nu_{max}^{KBr}$ cm$^{-1}$: 1775, 1680, 1620.

NMR (D$_2$O)δ: 1.65(3H, d, J=7.0 Hz, 2α—C$\underline{H}_3$), 2.60 to 3.00(6H, m, —C$\underline{H}_2$C$\underline{H}_2$N<, morpholine methylene 3- and 5-positions), 3.70 to 3.96(4H, m, morpholine methylene 2- and 6-positions), 4.00 (2H, s, —C$\underline{H}_2$—CO—), 4.16 to 4.60(3H, m, —OC$\underline{H}_2$C$\underline{H}_2$—2β-$\underline{H}$), 5.43(1H, d, J=5.0 Hz, 6-$\underline{H}$), 5.85(1H, d, J=5.0 Hz, 7-$\underline{H}$), 7.10 to 7.30(2H, m, thiophene proton(3- and 4-positions)), 7.35 to 7.55(1H, m, thiophene proton (5-position)).

Elemental analysis, for C$_{21}$H$_{25}$N$_4$O$_6$S$_2$Na.2H$_2$O: Calcd.: C 45.64; H 5.29; N 10.14; S 11.60; Found: C 45.83, H 5.26; N 9.98; S 11.58.

EXAMPLE 44

Diphenylmethyl 7-amino-2α-methyl-3-methoxyiminomethylceph-3-em-4-carboxylate

A 5 ml portion of pyridine was added to a solution of 2.8 g of diphenylmethy 7-(2-thienylacetamido)-2α-methyl-3-methoxyiminomethylceph-3-em-4-carboxylate in 60 ml of CH$_2$Cl$_2$, and 3.05 g of PCl$_3$ was then added to the mixture at −10° C. under a stream of nitrogen, followed by stirring at the same temperature for 1 hour. After adding 50 ml of MeOH in once, the mixture was stirred at from −15° to −10° C. for 30 minutes and further at room temperature for 2 hours. Following addition of 100 ml of 0.5M K$_2$HPO$_4$ solution, the reaction solution was adjusted to pH 2.0 with 25% H$_3$PO$_4$, and stirred for 30 minutes to separate out the CH$_2$Cl$_2$ layer. The CH$_2$Cl$_2$ layer was washed with saturated aqueous NaCl solution, and dried over MgSO$_4$, followed by distilling off the CH$_2$Cl$_2$ under reduced pressure. The residue was added on a column of silica gel, and the fractions eluted with CH$_2$Cl$_2$.AcOEt (35:1) were collected to distill off the solvent under reduce pressure, thus yielding 1.44 g (66%) of diphenylmethyl 7-amino-2α-methyl-3-methoxyiminomethylceph-3-em-4-carboxylate.

IR $\nu_{max}^{KBr}$ cm$^{-1}$: 1785, 1735.

NMR (DMSO-d$_6$+D$_2$O)δ: 1.54(3H, d, J=7.5 Hz, 2α—C$\underline{H}_3$), 3.83(3H, s, —OC$\underline{H}_3$), 4.31(1H, q, J=7.5 Hz, 2β-$\underline{H}$), 4.98(1H, d, J=5.0 Hz, 6-$\underline{H}$), 5.26(1H, d, J=5.0 Hz, 7-$\underline{H}$), 6.94(1H, s, —C$\underline{H}$(C$_6$H$_5$)$_2$), 7.38(10H, s, C$_6$$\underline{H}_5$x2), 7.93(1H, s, —C$\underline{H}$=N—).

Elemental analysis, for C$_{23}$H$_{23}$N$_3$O$_4$S: Calcd.: C 63.14; H 5.30; N 9.61; S 7.33; Found: C 63.34; H 5.37; N 9.32; S 7.34.

EXAMPLE 45

Diphenylmethyl 7-[2-phenyl-(Z)-2-methoxyiminoacetamido]-2α-methyl-3-methoxyiminomethylceph-3-em-4-carboxylate A 240 mg quantity of dicyclohexylcarbodiimide was added to a solution of 179 mg of Z-2-methoxyiminophenylacetic acid and 437 mg of diphenylmethyl 7-amino-2α-methyl-3-methoxyiminomethylceph-3-em-4-carboxylate in 30 ml of CH$_2$Cl$_2$ at −10° C., and the mixture was stirred at the same temperature for 1 hour and then at room temperature overnight. The resultant dicyclohexyl urea was filtered out, and the filtrate was washed with 5% aqueous NaHCO$_3$, 5% H$_3$PO$_4$ and saturated aqueous NaCl solution, successively, and dried over MgSO$_4$ to distill off the CH$_2$Cl$_2$ under reduced pressure. The residue was added on a column of silica gel, and the fractions eluted with CH$_2$Cl$_2$ were collected, followed by distilling off the CH$_2$Cl$_2$ under reduced pressure, thus yielding 488 mg (82%) of diphenylmethyl 7-[2-phenyl-(Z)-2-methoxyiminoacetamido]-2α-methyl-3-methoxyiminomethylceph-3-em-4-carboxylate.

IR $\nu_{max}^{KBr}$ cm$^{-1}$: 1795, 1725, 1670.

NMR (DMSO-d$_6$)δ: 1.56(3H, d, J=7.0 Hz, 2α—C$\underline{H}_3$), 3.82(3H, s, —OC$\underline{H}_3$), 3.93(3H, s, —OC$\underline{H}_3$), 4.37(1$\underline{H}$, q, J=7.0 Hz, 2β-$\underline{H}$), 5.47 (1H, d, J=5.0 Hz, 6-$\underline{H}$), 6.07(1H, dd, J=5.0, 8.0 Hz, 7-$\underline{H}$), 6.93(1H, s, —C$\underline{H}$(C$_6$H$_5$)$_2$), 7.15 to 7.77(15H, m, C$_6$$\underline{H}_5$x3), 7.93(1H, s, —C$\underline{H}$=N—).

Elemental analysis, for C$_{32}$H$_{30}$N$_4$O$_6$S: Calcd.: C 64.20; H 5.05; N 9.36; S 5.36; Found: C 64.35; H 5.14; N 9.12; S 5.48.

EXAMPLE 46

7-[2-Phenyl-(Z)-2-methoxyiminoacetamido]-2α-methyl-3-methoxyiminomethylceph-3-em-4-carboxylic acid A solution of 294 mg of diphenylmethyl 7-[2-phenyl-(Z)-2-methoxyiminoacetamido]-2α-methyl-3-methoxyiminomethylceph-3-em-4-carboxylate in 0.3 ml of anisole and 10 ml of CF$_3$COOH was stirred at room temperature for 20 minutes. After distilling off the CF$_3$COOH under reduced pressure, the residue was dissolved in AcOEt and then transferred into 5% aqueous NaHCO$_3$. The water layer was adjusted to pH 2.0 with 5% H$_3$PO$_4$ added, and extracted again with AcOEt. The AcOEt layer was washed with H$_2$O and saturated aqueous NaCl solution, successively, and dried over Na$_2$SO$_4$, followed by distilling off the AcOEt under reduced pressure. The residue was treated with Et$_2$O, thus yielding 114 mg (54%) of 7-[2-phenyl-(Z)-2-methoxyiminoacetamido]-2α-methyl-3-methoxyiminomethylceph-3-em-4-carboxylic acid as crystals.

m.p. 189° C. (decomp.).

IR $\nu_{max}^{KBr}$ cm$^{-1}$: 1795, 1730, 1650.

NMR (DMSO-d$_6$)δ: 1.56(3H, d, J=7.0 Hz, 2α—C$\underline{H}_3$), 3.86(3H, s, —OC$\underline{H}_3$), 3.92(3H, s, —OC$\underline{H}_3$), 4.32(1$\underline{H}$, q, J=7.0 Hz, 2β-$\underline{H}$), 5.43(1H, d, J=5.0 Hz, 6-$\underline{H}$), 5.98(1H, dd, J=5.0, 8.0 Hz, 7-$\underline{H}$), 7.30 to 7.70(5H, m, C$_6$H$_5$), 8.09(1H, s, —C$\underline{H}$=N—), 9.81(1H, d, J=8.0 Hz, —CO—N$\underline{H}$—).

Elemental analysis, for C$_{19}$H$_{20}$N$_4$O$_6$S: Calcd.: C 52.77; H 4.66; N 12.96; S 7.41; Found: C 52.71; H 4.63; N 12.95; S 7.30.

EXAMPLE 47

Diphenylmethyl 7-[2-(2-choloroacetylaminothiazol-4-yl)-(Z)-2-methoxyiminoacetamido]-2α-methyl-3-methoxyiminomethylcheph-3-em-4-carboxylate To a solution of 656 mg of diphenylmethyl 7-amino-2α-methyl-3-methoxyiminomethylceph-3-em-4-carboxylate in 30 ml of CH$_2$Cl$_2$ were added, at −20° C., 0.2 ml of Et$_3$N and 407 mg of 2-(2-chloroacetylaminothiazol-4-yl)-(Z)-2-methoxyiminoacetylchloride, and the mixture was stirred at from −20° C. to −15° C. for 1.5 hours. The reaction solution was washed with H$_2$O, 5% aqueous NaHCO$_3$ and saturated aqueous NaCl solution, successively, and dried over MgSO4, followed by distilling off the CH2Cl2 under reduced pressure. The residue was added on a column of silica gel, and the fractions eluted with CH2Cl2.AcOEt (15:1) were collected to distill off the solvent under reduced pressure, thus yielding 783 mg (75%) of diphenylmethyl 7-[2-(2-chloroacetylaminothiazol-4-yl)-(Z)-2-methoxyiminoacetamido]-2α-methyl-3-methoxyiminomethylceph-3-em-4-carboxylate.

Beilstein reaction: Positive.

IR $\nu_{max}^{KBr}$ cm$^{-1}$: 1795, 1730, 1690.

Elemental analysis, for C31H29N6O7S2Cl: Calcd.: C 53.40; H 4.19; N 12.06; S 9.20; Found: C 53.33; H 4.01; N 11.95; S 9.13.

EXAMPLE 48

Diphenylmethyl 7-[2-(2-aminothiazol-4-yl)-(Z)-2-methoxyiminoacetamido]-2α-methyl-3-methoxyiminomethylceph-3-em-4-carboxylate A solution of 84 mg of thiourea in 1 ml of H2O was added to a solution of 713 mg of diphenylmethyl 7-[2-(2-chloroacetylaminothiazol-4-yl)-(Z)-2-methoxyiminoacetamido]-2α-methyl-3-methoxyiminomethylceph-3-em-4-carboxylate in 10 ml of tetrahydrofuran, and the mixture was stirred overnight to distill off the solvent under reduced pressure. The residue was dissolved in CH2Cl2, washed with H2O and saturated aqueous NaCl solution, successively, and dried over MgSO4, followed by distilling off the CH2Cl2 under reduced pressure. The residue was added on a column of silica gel, and the fractions eluted with CH2Cl2.acetone (9:1) were collected to distill off the solvent, thus yielding 180 mg (28%) of diphenylmethyl 7-[2-(2-aminothiazol-4-yl)-(Z)-2-methoxyiminoacetamido]-2α-methyl-3-methoxyiminomethylceph-3-em-4-carboxylate.

IR $\nu_{max}^{KBr}$ cm$^{-1}$: 1800, 1740, 1695.

NMR (DMSO-d6+D2O)δ: 1.54(3H, d, J=7.0 Hz, 2α—C$\underline{H}$3), 3.82(3H, s, —OC$\underline{H}$3), 3.85(3H, s, —OC$\underline{H}$3), 4.36(1$\underline{H}$, q, J=7.0 Hz, 2β-$\underline{H}$), 5.41(1H, J=5.0 Hz, 6-$\underline{H}$), 5.99(1H, d, J=5.0 Hz, 7-$\underline{H}$), 6.74(1H, s, thiazole 5-$\underline{H}$), 6.92(1H, s, —C$\underline{H}$(C6H5)2)̄, 7.36(10H, s, C6H5x2).

Elemental analysis, for C29 H28N6O6S2: Calcd.: C 56.11; H 4.55; N 13.54; S 10.33; Found: C 56.20; H 4.79; N 13.07; S 9.95.

EXAMPLE 49

Sodium 7-[2-(2-aminothiazol-4-yl)-(Z)-2-methoxyiminoacetamido]-2α-methyl-3-methoxyiminomethylceph-3-em-4-carboxylate A solution of 139 mg of diphenylmethyl 7-[2-(2-aminothiazol-4-yl)-(Z)-2-methoxyiminoacetamido]-2α-methyl-3-methoxyiminomethylceph-3-em-4-carboxylate in 0.15 ml of anisole and 10 ml of CF3COOH was stirred at room temperature for 20 minutes. After distilling off CF3COOH under reduced pressure, the residue was distributed in Et2O and 5% aqueous NaHCO3 to separate out the water layer. The water layer was adjusted to pH 7.0 with 5% H3PO4 added, and then added on a column of Amberlite XAD-II (produced by Rohm & Haas). After washing the column with water, the fractions eluted with 10% aqueous MeOH were collected, concentrated under reduced pressure and freeze-dried, thus yielding 84 mg (73%) of sodium 7-[2-(2-aminothiazol-4-yl)-(Z)-2-methoxyiminoacetamido]-2α-methyl-3-methoxyiminoethylceph-3-em-4-carboxylate.

IR $\nu_{max}^{KBr}$ cm$^{-1}$: 1775, 1675.

NMR (D2O)δ: 1.70(3H,d,J=7.0 Hz,2α—C$\underline{H}$3), 4.00(3H,s,—OC$\underline{H}$3) 4.10(3H,s,—OC$\underline{H}$3, 4.37(1H,q,J=7.0 Hz,2β-$\underline{H}$), 5.53(1H,d,J=4.5 Hz, 6-$\underline{H}$), 6.02(1H,d,J=4.5 Hz,7-$\underline{H}$), 7.10(1H,s,thiazole, 5-$\underline{H}$), 8.15(1H,s,—C$\underline{H}$=N—).

Elemental analysis, for C16H17N6O6S2Na.2H2O: Calcd.: C 37.50; H 4.13; N 16.40; S 12.51; Found: C 37.81; H 4.14; N 16.78; S 12.22.

We claim:

1. A process for producing a ceph-2-em derivative of the formula:

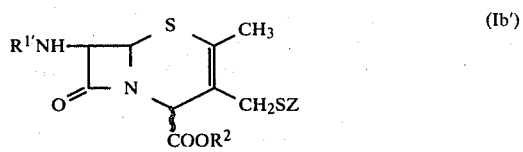

wherein R$^{1'}$ is an acyl group represented by the following formula:

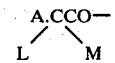

wherein A is phenyl, thienyl or 2-aminothiazol group; L is hydrogen, amino or N-lower-alkyl-2,3-dioxo-1-piperazinylcarboxamide group; M is hydrogen; and L and M combine to be =N—OB group (B is a lower alkyl group); —COOR$^2$ is a carboxyl group or esterified carboxyl group; and Z is a heterocyclic group selected from the group consisting of thiadiazolyl, tetrazolyl, triazolyl, oxadiazolyl, oxazolyl, thiazolyl, thiazolinyl, pyridyl, pyridazinyl and tetrazolopyridazinyl, or said heterocyclic group substituted by substituents selected from the group consisting of lower alkyl groups, lower alkyl groups substituted by hydroxy, carboxy, dimethylamino or sulfo, mercapto groups, hydroxy group, amino group, lower alkylthio groups and lower alkoxy groups; or a pharmaceutically acceptable salt thereof, which comprises reacting a ceph-2-em derivative of the formula:

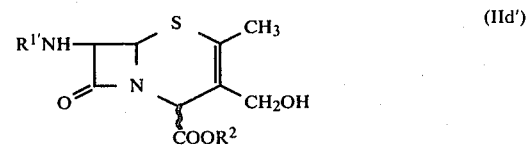

wherein R$^{1'}$ and —COOR$^2$ have the same meaning as above, or a pharmaceutically acceptable salt thereof, with a halogenating agent, and then with a heterocyclic thiol compound or a substituted heterocyclic thiol compound of the formula: ZSH, wherein Z has the same meaning as defined above or a pharmaceutically acceptable salt thereof to produce the ceph-2-em derivative of formula (Ib').

2. A process for producing a ceph-3em derivative of the formula:

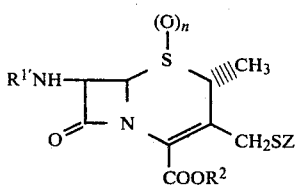

wherein R¹' is an acyl group represented by the following formula:

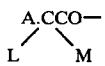

wherein A is phenyl, thienyl or 2-aminothiazolyl group; L is hydrogen, amino or N-lower-alkyl-2,3-dioxo-1-piperazinylcarboxamide group; M is hydrogen; and L and M combine to be =N—OB group (B is a lower alkyl group); —COOR² is a carboxyl group or esterified carboxyl group; Z is a heterocyclic group selected from the group consisting of thiadiazolyl, tetrazoyl, triazolyl, oxadiazolyl, oxazolyl, thiazolyl, thiazolinyl, pyridyl, pyridazinyl and tetrazolopyridazinyl, or said heterocyclic group substituted with substituents selected from the group consisting of lower alkyl groups, lower alkyl groups substituted by hydroxy, carboxy, dimethylamino or sulfo, mercapto groups, hydroxy group, amino group, lower alkylthio groups and lower alkoxy groups; and n is 0 or 1; or a pharmaceutically acceptable salt thereof, which comprises oxidizing with a peracid selected from the group consisting of performic acid, peracetic acid, permaleic acid, perbenzoic acid, m-chloro-perbenzoic acid, monoperphthalic acid, p-toluenepersulfonic acid, persulfonic acid, hydrogen peroxide, periodic acid and persulfuric acid, a ceph-2-em derivative of the formula:

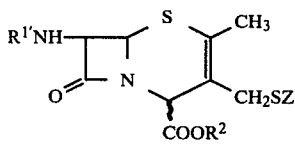

wherein R¹', —COOR² and Z have the same meaning as above, or a pharmaceutically acceptable salt thereof.

3. A process for producing a ceph-2-em derivative of the formula:

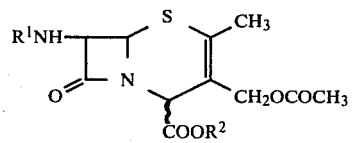

wherein R¹ is an acyl group represented by the following formula:

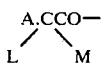

wherein A is phenyl, thienyl or 2-aminothiazolyl group; L is hydrogen, amino or N-lower-alkyl-2,3-dioxo-1-piperazinylcarboxamide group; M is hydrogen; and L and M combine to be =N—OB group (B is a lower alkyl group); and —COOR² is a carboxyl group or esterified carboxyl group; or a pharmaceutically acceptable salt thereof, which comprises reacting a ceph-3-em derivative of the general formula:

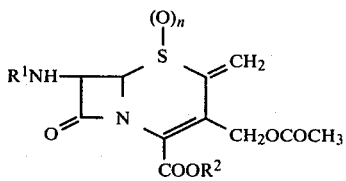

wherein R¹ and —COOR² have the same meaning as above and n is 0 or 1; or a pharmaceutically acceptable salt thereof with an alkali metal borohydride.

4. A process for producing a 2β-methyl-3-acetoxymethyl-ceph-3-em derivative of the formula:

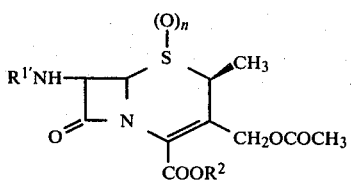

wherein R¹' is an acyl group represented by the following formula:

wherein A is phenyl, thienyl or 2-aminothiazolyl group; L is hydrogen, amino or N-lower-alkyl-2,3-dioxo-1-piperazinylcarboxamide group; M is hydrogen; and L and M combine to be =N—OB group (B is a lower alkyl group); —COOR² is a carboxyl group or esterified carboxyl group; and n is 0 or 1; or a pharmaceutically acceptable salt thereof, which comprises oxidizing with a peracid selected from the group consisting of performic acid, peracetic acid, permaleic acid, perbenzoic acid, m-chloro-perbenzoic acid, monoperphthalic acid, p-toluenepersulfonic acid, persulfonic acid, hydrogen peroxide, periodic acid and persulfuric acid, a ceph-2-em derivative of the formula:

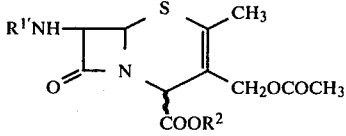

wherein R¹' and —COOR² have the same meaning as above, or a pharmaceutically acceptable salt thereof.

5. A process for producing a ceph-3-em derivative of the formula:

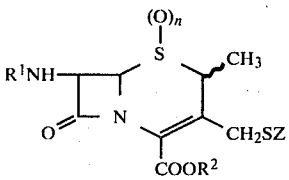

wherein R¹ is hydrogen or an acyl group represented by the following formula:

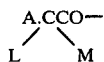

wherein A is phenyl, thienyl or 2-aminothiazolyl group; L is hydrogen, amino or N-lower-alkyl-2,3-dioxo-1-piperazinylcarboxamide group; M is hydrogen; and L and M combine to be =N—OB group (B is a lower alkyl group); —COOR² is carboxyl group or esterified carboxyl group; Z is a heterocyclic group selected from the group consisting of thiadiazolyl, tetrazoyl, triazolyl, oxadiazolyl, oxazolyl, thiazolyl, thiazolinyl, pyridyl, pyridazinyl and tetrazolopyradazinyl, or said heterocyclic group; substituted with substituents selected from the group consisting of lower lower alkyl groups, lower alkyl groups substituted by hydroxy, carboxy, dimethylamino or sulfo, mercapto groups, hydroxy group, amino group, lower alkylthio groups and lower alkoxy groups; and n is 0 or 1; or a pharmaceutically acceptable salt thereof, which comprises reacting a ceph-3-em derivative of the formula:

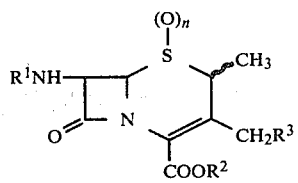

wherein R¹, —COOR² have the same meaning as above; R³ is halogen; and n is 0 or 1; or a pharmaceutically acceptable salt thereof with a heterocyclic thiol compound or substituted heterocyclic thiol compound of the formula ZSH wherein Z has the same meaning as defined above, or a pharmaceutically acceptable salt thereof.

6. A process for producing a ceph-3-em derivative, as claimed in claim 5, wherein a ceph-3-em derivative is 7-[2-(2-aminothiazol-4-yl)-(z)-2-methoxyiminoacetoamido]-2β-methyl-3-(1-methyl-1H-tetrazol-5-yl)thiomethylceph-3-em-4-carboxylic acid, or a pharmaceutically acceptable salt thereof.

7. A process for producing a 2α-methyl-ceph-3-em derivative of the formula:

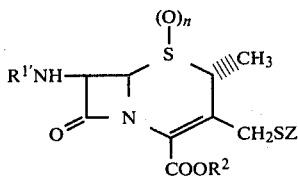

wherein R¹' is an acyl group represented by the following formula:

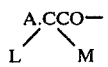

wherein A is phenyl, thienyl or 2-aminothiazolyl group; L is hydrogen, amino or N-lower-alkyl-2,3-dioxo-1-piperazinylcarboxamide group; M is hydrogen; and L and M combine to be =N—OB group (B is a lower alkyl group); —COOR² is a carboxyl group or esterified carboxyl group, Z is a heterocyclic group selected from the group consisting of thiadiazolyl, tetrazoyl, triazolyl, oxadiazolyl, oxazolyl, thiazolyl, thiazolinyl, pyridyl, pyridazinyl and tetrazolopyridazinyl, or said heterocyclic group substituted with substituents selected from the group consisting of lower alkyl groups, lower alkyl groups substituted by hydroxy, carboxy, dimethylamino or sulfo, mercapto groups, hydroxy group, amino group, lower alkylthio groups and lower alkoxy groups; n is 0 or 1, or a pharmaceutically acceptable salt thereof which comprises reacting a ceph-3-em derivative of the formula:

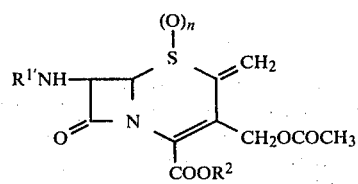

wherein R¹', —COOR² and n have the same meanings as defined above, with zinc-formic acid, then hydrolyzing the resulting compound of the formula:

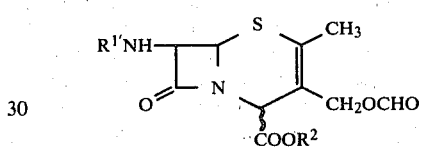

wherein R¹' and —COOR² have the same meanings as defined above, and reacting the resulting compound of the formula:

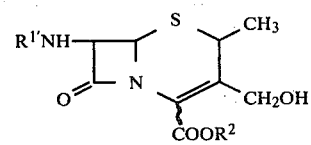

wherein R¹' and —COOR² have the same meanings as defined above, with a halogenating agent, and then with a compound of the formula:

ZSH wherein Z has the same meaning as defined above, and oxidizing the resulting compound of the formula:

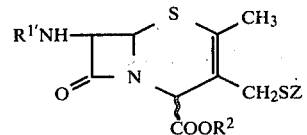

wherein R¹', Z and —COOR² have the same meanings as defined above with a peracid selected from the group consisting of performic acid, peracetic acid, permaleic acid, perbenzoic acid, m-chloro-perbenzoic acid, monoperphthalic acid, p-toluenepersulfonic acid, persulfonic acid, hydrogen peroxide, periodic acid and persulfuric acid.

8. A process for producing a 2β-methyl-3-acetoxymethylceph-3-em derivative of the formula:

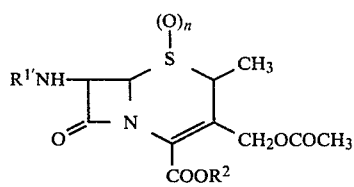

wherein R¹′ is an acyl group represented by the following formula:

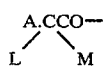

wherein A is phenyl, thienyl or 2-aminothiazolyl group; L is hydrogen, amino or N-lower-alkyl-2,3-dioxo-1-piperazinylcarboxamide group; M is hydrogen; and L and M combine to be =N—OB group (B is a lower alkyl group); —COOR² is a carboxyl group is esterified carboxyl group, n is 0 or 1, or a pharmaceutically acceptable salt thereof which comprises reacting a ceph-3-em derivative of the formula:

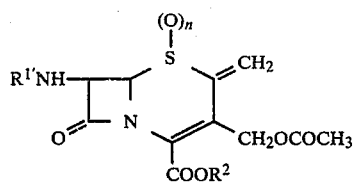

wherein R¹′, —COOR² and n have the same meanings as defined above, with an alkali metal borohydride, and oxidizing the resulting compound of the general formula:

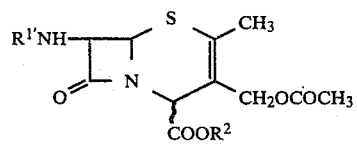

wherein R¹′ and —COOR² and n have the same meanings as defined above with a peracid selected from the group consisting of performic acid, peracetic acid, permaleic acid, perbenzoic acid, m-chloro-perbenzoic acid, monoperphthalic acid, p-toluenepersulfonic acid, persulfonic acid, hydrogen peroxide, periodic acid and persulfuric acid.

9. A process for producing a ceph-2-em derivative or a pharmaceutically acceptable salt thereof as claimed in claim 1, wherein the ester group of the esterified carboxyl group is tert-butyl, 2,2,2-trichloroethyl, benzyl, p-methoxyl, p-nitrobenzyl, trityl, benzhydryl, bis(p-methoxyphenyl)methyl, phenacyl, 2-methylthioethyl, trimethylsilyl, dimethylsilyl, alkoxymethyl, 1-alkoxyethyl, alkylthiomethyl, acetoxymethyl, pivaloyloxymethyl, 1-n-propionyloxyethyl, 1-alkoxycarbonyloxyethyl or phthalidyl, and the halogenating agent is selected from phosphorus trihalide, phosphoryl halide and thionyl halide.

10. A process for producing a ceph-3-em derivative or a pharmaceutically acceptable salt thereof as claimed in claim 2, wherein the ester residue of the carboxyl group is tert-butyl, 2,2,2-trichloroethyl, benzyl, p-methoxyl, p-nitrobenzyl, trityl, benzhydryl, bis(p-methoxyphenyl)methyl, phenacyl, 2-methylthioethyl, trimethylsilyl, dimethylsilyl, alkoxymethyl, 1-alkoxyethyl, alkylthiomethyl, acetoxymethyl, pivaloyloxymethyl, 1-n-propionyloxyethyl, 1-alkoxycarbonyloxyethyl or phthalidyl.

11. A process for producing a ceph-2-em derivative or a pharmaceutically acceptable salt thereof, as claimed in claim 3, wherein the ester residue of the esterified carboxyl group is tert-butyl, 2,2,2-trichloroethyl, benzyl, p-methoxyl, p-nitrobenzyl, trityl, benzhydryl, bis(p-methoxyphenyl)methyl, phenacyl, 2-methylthioethyl, trimethylsilyl, dimethylsilyl, alkoxymethyl, 1-alkoxyethyl, alkylthiomethyl, acetoxymethyl, pivaloyloxymethyl, 1-n-propionyloxyethyl, 1-alkoxycarbonyloxyethyl or phthalidyl.

12. A process for producing a 2β-methyl-3-acetoxymethyl-ceph-3em derivative or a pharmaceutically acceptable salt thereof, as claimed in claim 4, wherein the ester residue of the esterified carboxyl group is tert-butyl, 2,2,2-trichloroethyl, benzyl, p-methoxyl, p-nitrobenzyl, trityl, benzhydryl, bis(p-methoxyphenyl)-methyl, phenacyl, 2-methylthioethyl, trimethylsilyl, dimethylsilyl, alkoxymethyl, 1-alkoxyethyl, alkylthiomethyl, acetoxymethyl, pivaloyloxymethyl, 1-n-propionyloxyethyl, 1-alkoxycarbonyloxyethyl or phthalidyl.

13. A process for producing a ceph-3-em derivative or a pharmaceutically acceptable salt thereof, as claimed in claim 5, wherein the ester group of the esterified carboxyl group is tert-butyl, 2,2,2-trichloroethyl, benzyl, p-methoxyl, p-nitrobenzyl, trityl, benzhydryl, bis(p-methoxyphenyl)methyl, phenacyl, 2-methylthioethyl, trimethylsilyl, dimethylsilyl, alkoxymethyl, 1-alkoxyethyl, alkythiomethyl, methyl, acetoxymethyl, pivaloyloxymethyl, 1-n-propionyloxyethyl, 1-alkoxycarbonyloxyethyl or phthalidyl.

14. A process for producing a 2α-methyl-ceph-3-em derivative or a pharmaceutically acceptable salt thereof as claimed in claim 7, wherein the ester group of the esterified carboxyl group is tert-butyl, 2,2,2-trichloroethyl, benzyl, p-methoxyl, p-nitrobenzyl, trityl, benzhydryl, bis(p-methoxyphenyl)methyl, phenacyl, 2-methylthioethyl, trimethylsilyl, dimethylsilyl, alkoxymethyl, 1-alkoxyethyl, alkylthiomethyl, acetoxymethyl, pivaloyloxymethyl, 1-n-propionyloxyethyl, 1-alkoxycarbonyloxyethyl or phthalidyl, and the halogenating agent is selected from phosphorus trihalide, phosphoryl halide and thionyl halide.

15. A process for producing a 2β-methyl-3-acetoxymethylceph-3-em derivative or a pharmaceutically acceptable salt thereof as claimed in claim 8, wherein the ester residue of the esterified carboxyl group is tert-butyl, 2,2,2-trichloroethyl, benzyl, p-methoxyl, p-nitrobenzyl, trityl, benzhydryl, bis(p-methoxyphenyl)-methyl, phenacyl, 2-methylthioethyl, trimethylsilyl, dimethylsilyl, alkoxymethyl, 1-alkoxyethyl, alkylthiomethyl, acetoxymethyl, pivaloyloxymethyl, 1-n-propionyloxyethyl, 1-alkoxycarbonyloxyethyl or phthalidyl.

* * * * *